United States Patent [19]

Hoitink

[11] Patent Number: 4,900,348
[45] Date of Patent: * Feb. 13, 1990

[54] PRODUCTION OF DISEASE SUPPRESIVE COMPOST AND CONTAINER MEDIA, AND MICROORGANISM CULTURE FOR USE THEREIN

[75] Inventor: Harry A. Hoitink, Wooster, Ohio

[73] Assignee: The Ohio State University Research Foundation, Columbus, Ohio

[ * ] Notice: The portion of the term of this patent subsequent to Feb. 10, 2004 has been disclaimed.

[21] Appl. No.: 11,831

[22] Filed: Feb. 6, 1987

Related U.S. Application Data

[63] Continuation-in-part of Ser. No. 757,389, Jul. 12, 1985, Pat. No. 4,642,131, which is a continuation-in-part of Ser. No. 519,691, Aug. 2, 1983, abandoned.

[51] Int. Cl.$^4$ .............................................. C05F 11/08
[52] U.S. Cl. ............................................... 71/6; 71/9; 71/12; 71/23; 71/24; 435/254; 435/850; 435/879; 435/945; 435/252.1; 435/252.4; 435/253.3
[58] Field of Search ............... 435/253, 254, 850, 874, 435/945; 71/5, 6, 9, 12, 23, 24

[56] References Cited

U.S. PATENT DOCUMENTS

| | | | |
|---|---|---|---|
| 2,034,678 | 3/1936 | Knaust et al. | 71/5 |
| 4,214,985 | 7/1980 | Bodenrader et al. | 71/2 |
| 4,642,131 | 2/1987 | Hoitink | 71/12 X |
| 4,678,669 | 7/1987 | Ricard . | |

OTHER PUBLICATIONS

Wolf et al., "The Fungi", 1947, p. 286-287.
G. C. Papavizas, "Trichoderma and Gliocladium: Biology, Ecology, and Potential for Biocontrol", Ann. Rev. Phytopath, 1985, 23:23–54.
Phytopathology, 1985, 75:1344, Abstracts 520 and 521.
Phytopathology, 1983, 73:1450–1456, G. A. Kuter, E. B. Nelson, H. A. J. Holtink; and L. V. Madden, "Fungal Populations in Container Media Amended with Composted Hardwood Bark Suppressive and Conductive to Rhizoctonia Damping-Off".
Phytopathology, 1983, 73:1457–1462, E. B. Nelson, G. A. Kuter, and H. A. J. Holtink, "Effects of Fungal Antagonists and Compost Age on Suppression of Rhizoctonia Damping-Off in Container Media Amended with Composted Hardwood Bark".

Primary Examiner—Ferris H. Lander
Attorney, Agent, or Firm—Sidney W. Millard

[57] ABSTRACT

Compost, e.g. hardwood bark, is rendered suppressive to plant pathogens, such as *Rhizoctonia solani*, *Pythium ultimum* and *Fusarium*, and/or diseases caused thereby by adding to the compost, desirably after peak heating has been achieved but before substantial recolonization of the compost by mesophilic microorganisms has occurred, one or more microorganisms antagonistic to the plant pathogen. Container media also is rendered suppressive to plant pathogens and/or diseases caused thereby by amending the media with the just-described prepared suppressive compost or, alternatively, by amending separately with the compost and with *Trichoderma* fungus and antagonistic bacterium separately or mixed together. Desirably, the inoculated antagonistic microorganisms comprise *Trichoderma hamatum* species A.T.C.C. No. 20765 or 20764, together with *Xanthomonas maltophilia* bacterium species A.T.C.C. No. 53199 or a *Flavobacterium balustinum* isolate 299, A.T.C.C. No. 53198 species, A.T.C.C. No. 53198.

16 Claims, 1 Drawing Sheet

FIG. 1

PRODUCTION OF DISEASE SUPPRESIVE COMPOST AND CONTAINER MEDIA, AND MICROORGANISM CULTURE FOR USE THEREIN

The United States Government has certain rights to this invention pursuant to Environmental Protection Agency Grant No. CR-810581-01-0.

This application is a continuation-in-part of my co-pending application Ser. No. 757,389, filed July 12, 1985, and issued Feb. 10, 1987 as Patent No. 4,642,131, which in turn was a continuation-in-part of my application Ser. No. 519,691 filed Aug. 2, 1983 and now abandoned.

BACKGROUND OF THE INVENTION

This invention relates to methods for the production of disease suppressive compost, as well as container media amended with such compost, and microorganism cultures for use in such methods. More particularly, this invention relates to methods for the production of disease suppressive compost in which one or more microorganisms antagonistic to plant pathogens are added to the compost, the timing of the addition of the microorganisms to the compost preferably being carefully controlled to produce the greatest suppression of the pathogens.

A variety of microorganisms, especially members of the genera Trichoderma and Pseudomonas, are antagonists to plant pathogens such as *Rhizoctonia solani, Pythium ultimum* and others. Furthermore, it is known that suppression of such pathogens in commercial crops such as radishes may be achieved by using on such crops a compost containing relatively high concentrations of the antagonistic microorganisms. However, hitherto it has not been possible to produce, in a reproducible manner, composts containing sufficient numbers of the antagonistic microorganisms. Composts produced in windows are typically recolonized, after peak heating, by large numbers of different microorganisms and, although some of these microorganisms are of antagonistic varieties, hitherto there has been no way of ensuring that the antagonistic microorganisms do achieve sufficient population densities to render the resulting compost suppressive to the plant pathogens.

Container media amended with composted hardwood tree bark (CHB) suppress Rhizoctonia damping-off (Rdo) (Nelson and Hoitink, 1982, Stephens, et al., 1981). Suppressiveness of CHB container media to Rdo varies with compost age and those amended with mature CHB (>11 weeks of composting) are most suppressive (Nelson and Hoitink, 1983). The suppressive effect lasts for at least 2 yrs. Container media with Canadian sphagnum peat as the sole organic component are conducive, although a source of light sphagnum peat has been described that may be suppressive for up to 7 weeks after planting.

Suppressiveness of CHB container media is microbial in nature (Nelson and Hoitink, 1982, 1983). Previous work with fungi isolated from suppressive and conducive CHB container media has shown that a relationship exists between population levels of certain fungi and Rdo suppression (Kuter et al, 1983). Isolates of *Trichoderma hamatum* (Bonord) Bain, aggr. and *T. harzianum* Rifai, the most abundant fungal taxa isolated from suppressive CHB container media (Kuter et al), are also the most efficacious fungi in inducing suppression to Rdo (Nelson et al 1983). The efficacy of *T. harzianum* is affected by the maturity level of CHB used in preparation of the container medium (Nelson et al 1983).

Container media amended with composts prepared from tree bark suppress a variety of soil-borne plant diseases including those caused by Pythium spp. (Plant and Soil 39: 591–602 (1973) Plant Dis. 64: 142–147 (1986), Annu. Rev. Phytopathol. 24: 93–114 (1986), Phytopathology 73: 274–278 (1983)). Container media that contain bark have largely replaced peat container media for production of nursery stock and some floral crops in the United States, Australia and European countries (Biocycle 25: 42–45 (1982)). Recycling of organic wastes into composts increasingly is chosen as a least objectionable procedure in dealing with waste problems. An increasing number of composts types, therefore, is becoming available to the ornamentals industry. The impact of composts on the soil microflora, plant pathogens and plant diseases is not well understood. More information is needed before effects of such amendments of container media are predictable.

The need for some method to produce sufficient populations of antagonistic microorganisms in compost, and also container media amended by the compost, is exacerbated by recent changes in commercial manufacture of compost. Until recently, most compost has been prepared in windrows or aerated piles exposed to weather. Recently, however, controlled processes using aerated silos or aerated tanks have been developed; in such processes, the material to be composted is placed in a substantially enclosed container through which air is forced in a controllable manner. Such processes allow better control over composting conditions and thus produce a more uniform product. Unfortunately, composts produced under such controlled conditions are normally recolonized after peak heating by a less diverse microflora than compost produced in windrows (Phytopathology 73: 1450–1456 (1983)), so that compost produced under such controlled conditions is less likely to be suppressive to plant pathogens.

Furthermore, with the increased attention being paid in recent years to reducing pollution of the environment, and more specifically pollution of surface waters, a large number of additional and/or refurbished sewage plants have been constructed. Such plants produce large quantities of sludge which must be disposed of, and the most convenient way to dispose of such sludge is composting followed by use of the composted sludge on agricultural land. However, the techniques used for composting sewage sludge in modern plants are not conducive to colonization of the sludge by antagonistic microorganisms which will render it suppressive to plant pathogens such as Rhizoctonia and Pythium. Consequently, if such composted sewage sludge is to be rendered suppressive to such pathogens, as is highly desirable where the composted sewage sludge is to be used for agricultural purposes, artificial inoculation of the composted sewage sludge with antagonistic microorganisms is necessary.

Finally, in view of the significant losses caused to various commercial crops by Rhizoctonia and Pythium, it is highly desirable that compost and container media should be suppressive to both these pathogens, and prior art methods do not yield composts and container media which are reliably suppressive to both pathogens.

It will thus be seen that there is a need for a method of reproducibly producing a compost suppressive to plant pathogens, and specifically a need for a method of reproducibly producing a compost and container media suppressive to both Rhizoctonia and Pythium. Furthermore, the method to be used for producing such suppressive compost should be usable in controlled composting processes, particularly those now used for composting sewage sludge, as well as in windrow or aerated pile composting processes. This invention seeks to provide methods for producing such suppressive composts and container media, and a microorganism culture for use in such methods.

SUMMARY OF THE INVENTION

As will be explained in more detail below, there have been isolated from soils fungi and bacteria which, when used in proper combinations in the inoculation of compost, are effective in rendering the compost suppressive to diseases caused by both *Rhizoctonia solani* and *Pythium ultimum*.

Accordingly, in one aspect this invention provides a biologically pure culture for inducing suppression of plant pathogens and/or diseases caused thereby in a compost, this culture consisting essentially of at least one Trichoderma fungus selected from the group consisting of *Trichoderma hamatum* isolate 382, A.T.C.C. No. 20765 and *T. hamatum* isolate 559, A.T.C.C. No. 20764, and at least one bacterium selected from the group consisting *Xanthomonas maltophilia* (*Pseudomonas maltophilia*) sp. isolate 76, A.T.C.C. No. 53199 and *Flavobacterium* sp. isolate 299, A.T.C.C. No. 53198.

In another aspect, the invention provides a biologically pure culture for inducing supression of plant pathogens and/or diseases caused thereby, this culture consisting essentially of any one or more of the following bacterium microorganisms: *Pseudomonas putida* isolate 315, A.T.C.C. No. 53915; *Pseudomonas stutzeri* isolate 280, A.T.C.C. No. 53917; *Pseudomonas fluorescens* biovar isolate A498, A.T.C.C. No. 53416 and the spontaneous rifampicin resistant mutants of each of *Flavobacterium balustinum* isolate 299, A.T.C.C. No. 53198, and (*Xanthomonas maltophilia* (*Pseudomonas maltophilia*) isolate 76, A.T.C.C. No. 53199, *Pseudomonas putida* isolate 315 A.T.C.C. No. 53915 biovar V A498. In still another aspect, the invention provides a biologically pure culture for inducing suppresssion of plant pathogens and/or diseases caused thereby, this culture consisting essentially of at least one Trichoderma fungus selected from the group consisting of *Trichoderma hamatum* isolates 382 and 599, A.T.C.C. Nos. 20765 and 20764 respectively, and at least one bacterium selected from the group of bacterium microorganisms recited in the just preceding statement.

In another aspect, this invention provides a method for producing a compost which is suppressive to at least *Rhizoctonia solani* and *Pythium ultimum* and/or diseases caused thereby, which method comprises inoculating into said compost at least one Trichoderma fungus selected from the group consisting of *Trichoderma hamatum* isolate 382, A.T.C.C. No. 20765 and *T. hamatum* isolate 559, A.T.C.C. No. 20764, and at least one bacterium selected from the group consisting of *Xanthomonas maltophilia* (*Pseudomonas maltophilia*) sp. isolate 76, A.T.C.C. No. 53199 and *Flavobacterium balustinum* sp. isolate 299, A.T.C.C. No. 53198.

In an additional aspect, the invention provides a method for producing a container medium, which is suppressive to at least *Rhizoctonia solani* and *Pythium ultimum* and/or diseases caused thereby, which method comprises amending the container medium so that each 100 parts thereof includes about 2.5 to 70 parts by volume of compost, e.g. prepared from hardwood tree bark, pine bark, or sewage sludge, and at least one Trichoderma fungus antagonistic to *Rhizoctonia solani* and at least one bacterium antagonistic to *Pythium ultimum* and suppressive to plant disease caused thereby with the amendment including at least 100 colony forming units each of the fungus and the bacterium for each gram dry weight of the compost. In one embodiment of this method, the amending of the container medium is with a compost which before amending has been suitably inoculated with the at least one fungus and the at least one bacterium. In an alternative embodiment of this method, the container medium amending is separately with the compost and with the fungus and bacterium separately or mixed together.

This invention also provides a biologically pure culture consisting essentially of any one or more of the following microorganisms:

*Trichoderma hamatum* isolate 382, A.T.C.C. No. 20765;

*Trichoderma hamatum* isolate 559, A.T.C.C. No. 20764;

*Xanthomonas maltophilia* (*Pseudomonas maltophilia*) sp. isolate 76, A.T.C.C. No. 53199; and

*Flavobacterium balustinum* isolate 299, A.T.C.C. No. 53198.

Furthermore, although it might at first appear that all that is necessary to produce a compost suppressive to diseases caused by plant pathogens is to introduce into the material being composted a sufficient quantity of an appropriate antagonistic microorganism, it has been found that this is not necessarily the case, and that unless the antagonistic microorganism is added at a particular time during the composting process, the population of the antagonistic microorganism or microorganisms in the compost may not increase to the levels necessary to make the entire compost suppressive. In particular, it has been found that the best results are obtained by adding the antagonistic microorganism or microorganisms to the material being composted after peak heating has been achieved but before substantial recolonization of the compost by mesophilic microorganisms has occurred.

Accordingly, this invention provides a method for producing a compost which is suppressive to a plant pathogen, and/or a disease caused thereby, this method comprising inoculating into the compost, after peak heating has been achieved but before substantial recolonization of the compost by mesophilic microorganisms has occurred, at least one microorganism suppressive to the plant disease.

As indicated by the A.T.C.C. reference numbers quoted above, preferred microorganisms for use in the cultures and methods of the present invention have all been deposited in the American Type Culture Collection, 12301 Parklawn Dr., Rockville, Md. 20852, under the deposit numbers quoted above. These deposits have been made under conditions that specify:

(a) access to the culture will be available during pendency of this patent application (or any continuation, division, or continuation-in-part thereof) to one determined by the Commissioner of Patents and Trademarks to be entitled thereto under U.S. Code Title 35, Section 122 and Code of Federal Regulations, Title 37, Section 1.14; and (b) that all restrictions on the availability to the public of the deposited culture will be irrevocably removed on the granting of a patent on any of the aforementioned applications.

DETAILED DESCRIPTION OF THE INVENTION

As already mentioned, the microorganism culture of the present invention comprises *Trichoderma hamatum*, isolate 382, A.T.C.C. No. 20765, or isolate 559, A.T.C.C. No. 20764 together with either *Xanthomonas maltophilia* (*Pseudomonas maltophilia*) sp. isolate 76, A.T.C.C. No. 53199 or *Flavobacterium balustinum* isolate 299, A.T.C.C. No. 53198. All four microorganisms were isolated by baiting composted hardwood bark and isolated by routine plating techniques which will be familiar to those skilled in the art. The biological characteristics of these microorganisms are as follows:

*T. hamatum* isolate 382, A.T.C.C. No. 20765 and isolate 559, A.T.C.C. No. 20764

Isolates 382 and 559 are not morphologically different and agree closely to the species description. The following description is based on observations of cultures produced on 2% malt extract agar (difco) at 22° C. under continuous light. Colonies expand rapidly and cover plates (9 cm. diameter) in one week. Abundant sporulation is evident across the surface of the cultures in 4 to 5 days. Conidia and conidiophores are produced in discrete pustules which are initially white but rapidly (1 to 2 days) turn green; unlike many other taxa in the genus Trichoderma, the conidiophores are relatively thick and conidiophore branches are short and crowded. The terminal end of each conidiophore is marked by the presence of an elongate, non-sporulating (i.e. sterile) undulating appendage. Phialides are borne on the verticillate conidiophore branches and conidia are produced in small clusters at the tip of each phialide. The conidia are oval, smooth and 3.5 to 4 by 2.5 microns in size.

*Xanthomonas maltophilia* (*Pseudomonas maltophilia*) sp. isolate 76, A.T.C.C. No. 53199

Straight or slightly curved rods, 0.5 by 1.5 microns, singly or in pairs. Gram-negative. Polar, multitrichous flaggelation. Oxidase and arginine Dihydrolase negative. Does not accumulate poly-beta-hydroxybutyrate as an intracellular carbon reserve. Colonies are yellowish. Does not produce fluorescent pigments on King's Medium B. Does not produce diffusable pigments on King's Medium A or nutrient agar. No denitrification. Strictly aerobic. Starch hydrolysis negative. Hydrogen sulfide from cysteine positive. Grows at 41° and 25° C. Hydrolyses casein, Tween 80 and gelatin. Lecithinase positive. Utilizes glucose and maltose as sole sources of carbon and energy only with the addition of the growth factors methionine, cystine, biotin, pantothenate and cyanocobalamin. Slight growth on glucose with addition of methionine or cystine alone.

*Flavobacterium balustinum* isolate 299, A.T.C.C. No. 53198

Rod-shaped cells with parallel sides and rounded ends, 0.5 microns wide and 1 to 3 microns long. Intracellular granules of poly-beta-hydroxybutyrate are absent. Gram-negative. Non-motile. Does not glide or spread. Aerobic, strictly respiratory. Does not grow at 41° C., grows at room temperature. Growth on nutrient agar is yellow-orange pigmented. Does not produce diffusable pigments on nutrient agar or King's Medium A. Does not fluoresce on King's Medium B. Colonies on nutrient agar (1 to 5 mm. diameter) are circular, translucent, smooth and shiny with entire edges. Oxidase positive and arginine dihydrolase negative. Acid is not produced under aerobic or anaerobic conditions from glucose. Does not utilize glucose as sole carbon and energy source without growth factors or with addition of methionine, cystine, nicotinate, glutamate, pantothenate, biotin and cyanocobalamin. Lecithinase positive. Starch, gelatin, casein and Tween 80 are hydrolyzed. Nitrate is not reduced and hydrogen sulfide is not produced from cysteine.

As will be apparent to those skilled in the art, commecial practice of the methods of the present invention will necessarily result in release of significant quantities of the inoculated microorganisms into the environment when the suppressive compost containing the microorganisms is spread on agricultural land. In view of certain disorders known to be associated with species of Pseudomonas, it is very doubtful whether current Environmental Protection Agency regulations will permit substantial release into the environment of the *Xanthomonas maltophilia* (*Pseudomonas maltophilia*) isolate used in the microorganism culture of the present invention, even though this isolate is not known to be associated with any pathogenic condition in plants. Accordingly, it is preferred that the bacteria used in the microorganism of the culture of the present invention be *Flavobacterium blaustinum* isolate 299, since the release of this Flavobacterium into the environment appears to pose no significant problems. Furthermore, experiments using composted hardwood bark, composted pine bark, and composted municipal sludge indicate that composts amended with this Flavobacterium and with either of the *Trichoderma hamatum* isolates 382 and 559 are suppressive not only to diseases caused by *Rhizoctonia solani* and *Pythium ultimum*, but are also consistently suppressive of Fusarium wilt caused by *Fusarium oxysporum* f. sp. *conglutinans* race 2 (Plant Disease 70: 1023–027 (1986)).

The term "biologically pure culture" is used herein in its conventional meaning of a culture in which substantially all of the microorganisms present are of the specified type or types i.e. one in which the microorganism population consists essentially of the specified type or tyeps of microorganisms. The term "biologically pure culture" does not, of course, exclude the presence of very small numbers of other microorganisms which may enter the culture, nor does it exclude the presence of substantial amounts of non-microorganism material, for example nutrient media and other additives needed to enable the microorganisms to be cultured. As will be known to those skilled in the art, cultures of bacteria are normally concentrated by centrifugation during the preparation of products intended for use in inoculating compost and such concentration procedures effectively remove the nutrient in culture media which could interfere with the suppressive activity of the antagonistic bacteria in compost. Such concentration steps should be employed in preparing bacteria-containing cultures of the present invention for inoculation. However, the present invention extends to the cultures both in forms containing nutrients and in concentrated forms from which the nutrients have effectively been removed.

The fungi and bacteria used in the biologically pure cultures of the invention may be cultured in media similar to those previously used for other species of Trichoderma, Pseudomonas and Flavobacterium. Thus, for example, the Trichoderma may be cultured on acidified potato-dextrose agar, while the bacteria may be cultured on nutrient agar or King's B medium.

In the preferred method of the invention for producing suppressive compost, in which the Trichoderma and the bacteria, e.g. the Pseudomonas or Flavobacterium, are inoculated into compost, the microorganisms may if desired be added separately. However, if it has been found more efficient to effect inoculation with a biologically pure culture containing the desired mixture of microorganisms. This method is applicable to a variety of composting materials, including composted hardwood bark, composted pine bark and composted sewage sludge. As already mentioned, the inoculation is desirably effected after peak heating has been achieved but before substantial recolonization of the compost by mesophilic microorganisms has occurred.

The quantity of microorganisms necessary to induce the required degree of suppressiveness in the resultant compost is easily determined by routine empirical tests, and may of course vary with the nature of the material being composted, the environment in which the compost is to be applied, the crop to be grown in the medium containing the compost (and in particular, susceptibility of the crop to the pathogens to which the compost is suppressive) and numerous other factors. However, in general it is preferred that at least about 100 colony forming units of each of the fungus and bacterium be added to each gram of dry weight of the composts, and in practice addition of from about $10^5$ to about $5 \times 10^7$ cells of each of the fungus and the bacterium to each gram dry weight of the compost appears to give optimum results.

As already mentioned, this invention also provides a method for producing a compost which is suppressive to a plant pathogen, which method comprises inoculating into the compost, after peak heating has been achieved but before substantial recolonization of the compost by mesophilic microorganism has occurred, at least one microorganism suppressive to the plant pathogen. The compost to be inoculated may be, for example, a composted hardwood bark, composted pine bark, or a composted sewage sludge. Desirably, there is inoculated into the compost at least one Trichoderma fungus antagonistic to *Rhizoctonia solani* and *Pythium ultimum* and the diseases caused by these pathogens and at least one bacterium antagonistic to diseases caused by *Pythium ultimum*. Also, desirably the combination of this fungus and bacterium renders the compost suppressive to disease caused by *Fusarium oxysporum* f.sp. *conglutinans* race 2.

Microorganisms other than those already mentioned may also be used even though much less effectively in this method of the invention. Thus, to produce compost suppressive of *Rhizoctonia solani*, the compost may be inoculated with fungi of the genera Trichloderma, Gliocladium, Penicillium, Mortierella, Paecilomyces, Geomyces, and Ophiostoma. Particularly preferred species of such fungi include *Trichoderma harzianum*, *T. viride*, *T. koningii*, *T. hamatum*, *Geomyces pannorum* var. *pannorum*, *G. pannorum* var. *asperulatus*, *Pennicillium montanense*, *P. griseofulvum*, *P. fellutinum*, *P. purpurogenum*, *P. ochrochloron*, *Mortierella vinacea*, *M. isabellina*, *M. zychae*, *M. alpina*, *Paecilomyces inflatus*, *Ophiostoma stenoceras* and *Gliocladium virens*.

When the material being composted is hardwood bark, the microorganism is desirably added to the composted material after it has been composted at least for about four months, although those skilled in the art will appreciate that the exact length of composting before the microorganisms should be added will vary somewhat with the composting conditions employed, including the exact nature of the hardwood bark being composted and the temperature and other environmental conditions under which the composting is effected.

A container medium is useful for growing plants and horticultural crops. A container medium (potting mix, potting soil, etc.) generally comprises one or more of light weight or neutral aggregates, such as silica sand, expanded shale, perlite, vermiculite, pumice, expanded polystyrene, and the like. Other container medium major constituents include Canadian, German, Michigan and other peats, composts, and/or sterilized soils, and also plant nutrients and trace elements as needed or desired. The amounts included of the aforementioned ingredients vary widely among various container media depending upon their ultimate utilization. Such prior art container media without suppressive compost added are conducive to Rhizoctonia and Pythium diseases (Ann. Rev. Phytophathol. 24: 93–114 (1986)).

In the invention there is provided or produced a container medium which is suppressive to at least *Rhizoctonia solani* and *Pythium ultimum* and/or medium on a volume basis so that each 100 parts thereof includes about 2.5 to parts of compost and at least one Trichoderma fungus antagonistic to *Rhizoctonia solani* and suppressive to plant disease caused thereby and at least on bacterium antagonistic to *Pythium ultimum* and suppressive to plant disease caused thereby with the amending including at least 100 colony formed units each of the fungus and the bacterium for each gram dry weight of the compost. Typically illustrative incorporated amounts of various different composts, expressed as percent by volume of the container medium, are for hardwood bark composts about 5 to 50%/v, pine bark compost about 20 to 70%/v, and sewage sludge compost about 2.5 to 40%/v.

In one method of producing the invention's container medium, the compost is pre-inoculated with the aforesaid antagonistic Trichoderma fungus and the antagonistic bacterium. In an alternative method, the container medium is amended separately with the compost and with said Trichoderma fungus and said baterium separately or mixed together.

The following Examples are now given, though by way of illustration only, to show details of particularly preferred microorganism cultures and methods of the present invention.

EXAMPLE 1

Experiments were conducted to determine the ability of composted hardwood bark to suppress *Rhizoctonia solani* after the bark had been inoculated at various stages during composting with isolates of various fungi obtained from previous hardwood bark composts.

A total of 331 fungal isolates were recovered by dilution plating and baiting procedures from a peat/perlite container medium amended with composted hardwood bark. The media used were amended with bark prepared in both aerated bins and windrows, and both the bin and field (windrow) compost were used in their conducive (green) and suppressive (mature) forms. Multiple cultures of the predominant fungal species isolated from the container medium were stored on potato dextrose agar slants at 4° C. for use in the experiments described below. The species of fungi isolated including the following:

Trichoderma harzianum
T. koningii
T. hamatum
T. viride
Geomyces pannorum var. pannorum
G. pannorum var. asperulatus
Penicillium montanese
P. ochrochloron
P. fellutinum
P. verrucosum var. cyclopium
P. griseolfulvum
Mortierella vinacea
M. isabellina
M. alpina
M. zychae
M. parvispora
M. zonata
Paecilomyces inflatus
Ophiostoma stenoceras
Gliocladium virens
Torulomyces lagena In addition, the isolates included an incompletely indentified Penicillium isolate identified as P. sp. 114, and an incompletely identified Geotrichum identified as G. sp. 36.

The ability of the resultant fungal isolates to induce suppression of Rhizoctonia solani in composted hardwood bark-amended container media was then tested as follows. Two types of composted hardwood bark were prepared, namely field composted hardwood bark obtained from windrows and bin composted hardwood bark obtained from a composting mass in an aerated bin. Different ages of bin compost were obtained by collecting 30 litter samples at three week intervals from a composting mass, the samples being stored at −7° C. until used in experiments. Green and mature field composted hardwood bark samples were obtained from windrows in a nursery. All the composted hardwood bark types were mixed with peat and perlite in a 5:3:2 v/v ratio as described in Nelson and Hoitink, Factors affecting suppression of Rhizoctonia solani in container media, Phytopathology, 72: 275-279 (1982). This mixture adjusts the air-filled pore space in the 10 cm. tall column used in the experiments described below to 15-20%. For certain experiments, similar media were prepared using fresh (uncomposted) hardwood bark in place of the composted hardwood bark.

Originally, it was planned to conduct tests using heated conducive (three week old) composted hardwood bark. However, preliminary experiments showed that addition of fungal isolates to this medium failed to yield consistent results, but that the necessary consistency could be substituted by using suppressive mature (44 week old) composted hardwood bark which had previously been rendered conductive by heating to 60° C. for five days. Accordingly, the heated mature composted hardwood bark medium was substituted for the proposed medium using heated conducive green hardwood bark.

For inoculation of these container media, spore suspensions of various funal isolates were prepared by growing cultures of the isolates on potato dextrose agar at 25° C. for 21 days, then placing the resultant colonized agar in 200 ml. of sterile distilled water, stirring the resultant mixture vigorously and filtering through two layers of cheesecloth. The filtrate was then centrifuged at 10,000 g. for ten minutes and the pellet which precipitaed resuspended in sterile tap water at pH 6.8. Spore concentrations were determined with a hemacytometer. The resultant aqueous spore suspension was then inoculated into the container media to produce final spore concentrations of $10^5$-$10^7$ colony forming units per gram dry weight of container medium.

An inoculum of Rhizoctonia solani in a chopped potato/soil mixture was prepared by a variant of the method described in Ko and Hora, A selective medium for the quantitative determination of Rhizoctonia solani in soil, Phytopathology, 61: 707-710 (1971), and the aforementioned paper in Phytopathology, 72: 275-279 (1982). To reduce variability in bioassays, the inoculum was prepared by grinding air-dried chopped potato/soil mixture in a mortar and pestle, followed by sieving through 2.0 mm and 1.0 mm sieves, the pieces remaining on the 1.0 mm sieve being used to infest the container media. This second sieve, which eliminated particles less than 1.0 mm in diameter, significantly increased the sensitivity of the assay described below. The R. solani inoculum was added to the spore-inoculated container medium at the rate of 0.6 g. of chopped potato/soil mixture per liter of container medium. A slow-release fertilizer was also added to the container medium, as described in the aforementioned paper in Phytopathology 72: 275-279 (1982). Following addition of the R. solani inoculum and the fertilizer, the samples were vigorously shaken to produce a truly homogeneous mixture.

The resultant mixture was then used in a variant of the Rhizoctonia damping-off assay described in Henis et al, Integrated Control of Rhizoctonia solani damping-off of radish: effect of successive planting, PCNB and Trichoderma harzianum on pathogen and disease, Phytopathology, 68: 900-907 (1978), this variant being described in the aforementioned paper in Phytopathology, 72: 275-279 (1982). The medium containing the bark, fungal spores and R. solani inoculum and fertilizer was placed in pots containing approximately 400 ml. of the amended container medium and 32 seeds of radish (Raphanus satius L., cultivar "Early Scarlet Globe", 97% germination) were placed in each pot. The seeds were covered with 1.0 cm of container medium and the pots incubated at 26° C. under a continuous illumination of 2,500 lux. The pots were saturated with tap water on alternate days and allowed to drain. After seven days, the number of healthy seedlings in each pot (five pots being used per treatment) was recorded and disease incidence (equal mean percentage of damped-off seedlings) determined.

In all experiments, container media amended with unheated suppressive bin comosted hardwood bark, and similar bark which had been heated to render it conducive, were included as controls not containing any fungal isolates.

Since the incidence of disease varied considerably in both the treated container media and the controls, in most cases the results below are standardized by expressing data as a percentage of the original suppressiveness (the control containing the unheated bark) eliminated by heat (as shown by the control containing the heated bark) which could be restored by adding the potential antagonist, the spore suspension of the fungal isolate. Thus, the percentage restoration of suppression given below was calculated using the formula:

%=100 (DH-DA)/(DH-D)

wherein:
DH is the disease incidence in the heated control;
DA is the disease incidence in the container medium amended with potential antagonist; and
D is the disease incidence in the container medium in the unheated control.

Each type of compost was prepared twice over a two year period and all experiments were repeated at least twice. Data were analyzed using simple t-tests, and analysis of variance and regression analysis where appropriate. Means were separated using the LSD test and Duncan's new multiple range test. The results are shown in Tables 1–4 below.

TABLE 1

Isolates From Suppressive Bin Compost

| Isolate | Mean percentage restoration of suppression |
|---|---|
| Trichoderma harzianum | 155.8 |
| Trichoderma koningii | 118.8 |
| Geomyces pannorum var. pannorum | 76.5 |
| Geomyces pannorum var. asperulatus | 55.9 |
| Penicillium ochrochloron | about 24 |
| Mortierella alpin | 20.9 |
| Mucor circinelloides | less than 20 |
| Torulomyces lagena | less than 20 |

TABLE 2

Conducive Bin Compost

| Isolate | Mean percentage restoration of suppression |
|---|---|
| Geomyces pannorum var pannorum | 48.8 |
| Paecilomyces inflatus | 48.2 |
| Ophiostoma stenoceras | 38.3 |
| Penicillium fellutinum | about 30 |
| Geomyces pannorum. var. asperulatus | about 28 |
| Penicillium ochrochloron | less than 20 |
| Botryotrichum piluliferum | less than 0 |
| Penicillium verrucosum var. cyclopium | less than −20 |
| Trichoderma harzianum | about −50 |
| Aspergillus fumigatus | about −130 |

TABLE 3

Suppressive Field Compost

| Isolate | Mean percentage restoration of suppression |
|---|---|
| Trichoderma hamatum | 81.5 |
| Penicillium montanese | 67.0 |
| Mortierella vinacea | about 32 |
| Geotrichum sp. 36 | about 26 |
| Penicillium ochrochloron | about 26 |
| Penicillium griseofulvum | about 26 |
| Penicillium sp. 114 | less than 20 |
| Chaetomium homopilatum | less than 20 |
| Chaetomium aureum | less than 20 |
| Mortierella parvispora | less than 10 |
| Mortierella isabellina | less than 0 |
| Trichoderma koningii | less than 0 |
| Geomyces pannorum var. pannorum | less than 0 |
| Penicillium purpurogenum | less than 0 |
| Ophiostoma stenoceras | about −20 |

TABLE 4

Conducive Field Compost

| Isolate | Mean percentage restoration of suppression |
|---|---|
| Mortierella vinacea | 52.8 |
| Penicillium ochrochloron | 50.9 |
| Mortierella isabellina | 34.2 |
| Ophiostoma stenoceras | 28.9 |
| Geomyces pannorum var. pannorum | 23.0 |
| Penicillium fellutinum | about 20 |
| Trichoderma koningii | less than 20 |
| Penicillium purpurogenum | less than 20 |
| Penicillium verrucosum var. cyclopium | less than 10 |
| Torulomyces lagena | less than 10 |

These experiments showed that a wide variety of the fungi recovered from container media amended with hardwood bark composts induced significant levels of suppression; however, in any given batch of amended medium only a small percentage of the above fungi were efficacious antagonists. Members of the genera Trichoderma, Gliocladium, Penicillium, Mortierella, Paecilomyces, Geomyces and Ophiostoma had the highest levels of antagonistic activity. The antagonistic activity of these genera is not surprising in view of reports in the literature of some of these genera as antagonists of R. solani as well as other root-infecting fungi; see for example Chet et al, Trichoderma hamatum: its hyphal interactions with Rhizoctonia solani and Pythium spp., Microbiol Ecology, 7: 29–38 (1981); Domsch et al, Compendium of Soil Fungi, Vol. 1, Academic Press, New York, 1980; and Tu and Vaartaja, The Effect of the Hyperparasite (Gliocladium virens) on Rhizoctonia solani and on Rhizoctonia root rot of white beans, Can. J. Bot., 59: 22–27 (1981). In general, fungal isolates from media amended with the three-week old conducive bin composts were generally not as antagonistic as isolates from media amended with suppressive bin composts (compare Tables 1 and 2); none of the isolates from the conducive media restored more than about 50% of the levels of suppression found in the unheated controls. In particular, isolates of Trichoderma harzianum and T. koningii from media amended with suppressive bin composts induced levels of suppression equal to or better than those found in media amended with the unheated suppressive composts (see Table 1). Isolates of Geomyces pannorum var. pannorum and asperulatus from media amended with suppressive bin compost also induced very significant levels of suppression.

The high levels of antagonistic activity of Trichoderma hamatum isolates recovered from media amended with suppressive field compost and the similarly high level of antagonistic activity of T. harzianum isolated from media amended with suppressive bin compost, coupled with the high population levels of these fungi observed experimentally, suggest that thest two Trichoderma fungi may be largely responsible for the suppression observed in some suppressive prior art composts.

A further series of experiments were conducted in the same manner except that the fungal isolates used were recovered from Rhizoctonia inocula (prepared in the manner described above) incubated in container media amended with suppressive or conducive composted hardwood bark. The results are shown in Tables 5 and 6 below.

TABLE 5

Media Amended with Suppressive Composted Hardwood Bark

| Isolate | Mean percentage restoration of suppression |
|---|---|
| Trichoderma hamatum | 149.9 |
| Trichoderma koningii | 98.7 |
| Gliocladium virens | 80.5 |
| Trichoderma harzianum | 43.6 |
| Mortierella zychae | 22.0 |
| Mortierella alpina | 21.6 |
| Humicola grisea | about 20 |
| No. 480 (unidentified) | less than 10 |
| Zygorrrhynchus moelleri | less than 10 |
| Mortierella parvispora | less than 10 |
| Mortierella zonata | less than 10 |
| No. 596 (unidentified) | less than 0 |
| Mortierella isabellina | less than 0 |

TABLE 6

Isolates from Inocula Incubated in Media Amended With Conducive Composted Hardwood Bark

| Isolate | Mean percentage restoration of suppression |
|---|---|
| Trichoderma harzianum | 67.4 |
| Ophiostoma stenocera | 39.4 |
| Gilmaniella humicola | about 22 |
| Aspergillus sp. 735 (incompletely identified) | about 20 |
| Botryotrichum piluliferum | less than 20 |
| Epichoccum purpurascens | less than 10 |
| Rhizopus oryzae | less than 10 |
| No. 596 | less than 0 |

From the data in Tables 5 and 6, it will be seen that Trichoderma species had the highest antagonistic activity of the fungi recovered from the inocula. Although the isolates from the media amended with the suppressive composted hardwood bark induced the greatest level of suppression (compare Tables 5 and 6) it was not possible to identify a consistent relationship between the levels of antagonistic activity and source when only single isolates of individual species were compared.

The antagonistic activities of 81 isolates of four species groups of Trichoderma isolated from media amended with suppressive and conducive composted hardwood bark were compared in the same manner as previous experiments by adding the isolates at the rate of 100,000 colony forming units per gram dry weight of container medium to media amended with mature composted hardwood bark heated to 60° C. The figures given in Table 7 below are % restoration; the variations shown are the 95% confidence intervals.

TABLE 7

Restoration of Suppression by Trichoderma Species Isolated from Suppressive or Conducive Container Media

| Species | No. of Isolates Tested | Conducive | Suppressive |
|---|---|---|---|
| T. hamatum | 25 | 50.9 + 19.9 | 77.3 + 26.1 |
| T. harzianum | 25 | 42.8 + 21.3 | 63.7 + 38.1 |
| T. koningii | 25 | 42.0 + 15.7 | 56.5 + 20.0 |
| T. viride | 6 | 28.1 + 14.9 | 36.7 + 53.8 |

Although the mean level of suppression induced by all species was apparently greater for isolates from media amended with suppressive composted hardwood bark than those amended with conducive hardwood bark, these differences were not significant at the 95% confidence level because of the high variability of isolates from a single source.

In a further series of experiments, increasing levels of a single isolate of Trichoderma harzianum were added to media amended with heated suppressive bin composted hardwood bark and unheated Canadian peat medium. Addition of only 100 colony forming units per gram dry weight of the composted hardwood bark amended media induced approximately 75% suppression of disease incidence, a level of suppression that was approximately equal to that induced by adding $10^8$ colony forming units per gram dry weight of the Canadian peat medium. Addition of 10,000 colony forming units per gram dry weight to the composted hardwood bark amended medium induced more than 90% suppression of disease incidence.

Experiments were also conducted to test whether the levels of suppression induced by Trichoderma harzianum in composted hardwood bark amended media varied with the age of the composted hardwood bark used. These experiments were conducted by adding 100 colony forming units per gram dry weight of a T. harzianum spore culture, produced as already described, to media amended with fresh and 3, 6 and 44 week-old composted hardwood bark. As is well known to those skilled in the art, hardwood bark composts relatively slowly, so that the three and six week old composted bark was still at the peak heating stage (which terminates at about 23 weeks) while the 44 week old bark was past the peak heating stage but not yet cooled to temperatures at which substantial recolonization by mesophilic microorganisms could be expected. Experiments were conducted using both unheated and heated mature composted hardwood bark as the amending agent and the results are shown in Table 8 below, where the columns headed 25° C. represent the unheated bark, while the columns headed 60° C. represent the bark which had previously been heated to this temperature for five days.

TABLE 8

Effect of Compost Age on The Induction of Suppression of Rhizoctonia Damping-off By Trichoderma harizanum

| | Disease Incidence | | | | | | | |
|---|---|---|---|---|---|---|---|---|
| | 25° C. Compost Age (weeks) | | | | 60° C. Compost Age (weeks) | | | |
| Trichoderma added | 0 | 3 | 6 | 44 | 0 | 3 | 6 | 44 |
| — | 79.2a | 79.9a | 70.8ab | 45.0b | 73.4ab | 85.7a | 73.0ab | 68.5ab |
| + | 73.7ab | 74.0ab | 58.1ab | 52.1ab | 53.6b | 68.2ab | 58.1b | 30.3c |

*Represents mean % damping-off after pre-incubating CHB-amended media with or without T. harzinanum; numbers followed by the same letter are not significantly (P = 0.05) different according to Duncan's new multiple range test.

The data in Table 8 show that only media amended with the mature, 44 week old composted hardwood bark were highly suppressive. As observed in the previous experiments, addition of *Trichoderma harzianum* to unheated mature composted hardwood bark amended medium did not significantly decrease damping-off. However, significantly higher levels of suppression (i.e. lower disease incidence) were induced by *Trichoderma harzianum* in heated mature composted hardwood bark amended media. Addition of this fungus had no significant effect on damping-off in media amended with fresh hardwood bark or the three or six week-old batches of composted hardwood bark regardless of whether or not these media has previously been heated.

In an attempt to determine whether the differences in levels of suppression induced in *Trichoderma harzianum* with age of compost used were related to differences in population level with age of compost used, further experiments were conducted to determine the population levels of *Trichoderma harzianum* in media amended with fresh (uncomposted) hardwood bark, and three, six and 44 week-old hardwood bark. These experiments showed that the differences in levels of suppression could not be due solely to differences in fungal population since after 14 days the population levels in the fresh and six-week old bark were substantially greater than those in the 44 week old bark, with the populations in the three week old bark being the lowest; after this 14-day period, the population in the fresh hardwood bark was approximately 5 million colony forming units per gram dry weight of compost, in the six week old bark approximately 10,000 CFU/g dry weight and in the three week old bark approximately 300 CFU/g dry weight. Regression analysis of the population data and comparison of slope values showed that the populations developed at a significantly lower rate in media amended with three or 44 week old bark than in media amended with fresh or six week old bark.

From all the foregoing experiments, it was concluded that the low level of suppression in media amended with green composted hardwood bark (whether bin or field) could not be attributed to the absence of antagonistic fungi or to low levels of antagonistic activity of isolates present in those media. Tables 1–6 above show that Trichoderma, as well as other fungi capable of restoring significant levels of suppression, were present in green as well as mature composted hardwood bark. Furthermore, Trichoderma isolates from media amended with green composted hardwood bark were almost as effective in inducing suppression as those isolated from media amended with mature composted hardwood bark (see Table 7 above). Furthermore, the foregoing experiments show that the low levels of disease suppression produced by conducive media are not due to limited population development of Trichoderma in such media, since the population levels obtained in media amended with fresh or six week old bark were actually greater than those obtained in the mature bark, yet suppression is significant in media amended with the mature bark (see Table 8 above). Rates of population growth were higher in the media amended with fresh or six-week old composted hardwood bark, but these media were conducive or only mildly suppressive. Therefore, disease suppression depends not only upon the presence of potential antagonistic microorganisms in composted hardwood bark amended media but also on factors which affect the activity of these organisms.

Although the activity of the antgonists were determined in media which had been heated 60° C. for five days and thus in which populations of competing microorganisms were reduced or eliminated, the results obtained with these heated media are likely to reflect those realized with antagonists in composts in the field because temperatures of around 60° C. are produced for several days after compost piles are turned; see, for example, Hoitink, Composted Hardwood Bark, A Lightweight Growth Medium with Fungicidal Properties, Plant Dis., 64: 142–147 (1980).

The foregoing results also show that by careful choice of the fungal antagonists used, the level of suppression in the antagonist-fortified mature compost amended medium can be significantly higher than in unfortified medium so that controlled production of suppressive container media has been rendered feasible.

As already mentioned, the three and six-week old composted hardwood bark had not yet passed through the peak heating stage, whereas the 44-week old bark has passed through the peak heating stage but has not yet undergone complete recolonization by mesophilic microorganisms. Accordingly, the foregoing experiments show that to produce the maximum antagonistic effect, the antagonistic microorganisms should be added to the compost after peak heating has been achieved but before substantial recolonization of the compost by mesophilic microorganisms has occured.

EXAMPLE 2

This Example illustrates the isolation of microorganisms useful in inducing suppression of disease caused by *Rhizoctonia solani* and *Pythium ultimum,* and processes for inducing suppression using the microorganisms isolated.

Potential antagonists were isolated from composted hardwood bark and sewage sludge by baiting the sludge with 1–2 mm. diameter inoculum pieces of *P. ultimum* embedded in suppressive batches of composted bark and sewage sludge. The pieces of inoculum were sandwiched between two layers of nylon screen and stapled together to prevent losses, approximately 50 pieces of inoculum being included in each sandwich. The inoculum pieces were buried in a container medium treated with the composted bark or sewage sludge, recovered from 0 to 40 days after burial and rinsed in sterile distilled water for 3 minutes to remove as many surface contaminants as possible. The inoculum pieces were then placed on acidified potato-dextrose agar for isolation of fungi, on yeast extract agar for isolation of actinomycetes and on nutrient agar and King's B medium for isolation of bacteria. After 48 hours incubation at room temperature on the acidified potato-dextrose agar, fungi were isolated from hyphal tips and transferred to potato-dextrose agar slants. Isolates of bacteria were streaked on nutrient agar for further purification.

The abilities of the potentially antagonistic microorganisms to induce suppression of Rhizoctonia or Pythium in various container media were tested by adding either fungal spores or bacterial cell suspensions to the test media and, on the following day, inoculating the test media with the pathogen and beginning an assay. Inocula for fungi were cultured on potato-dextrose agar plates 9 cm. in diameter for 14–21 days. Spores were collected by placing the colonized agar in 200 ml. of water and vigorously shaking the flasks. The water containing the spores was decanted, filtered through cheesecloth and the spores were then washed by centrifugation. The resultant pellets were resuspended in water and spore concentrations were determined using a hemacytometer in order to ensure a uniform inoculum density for each fungus. In these assays, $10^5$–$10^6$ spores per gram dry weight of container medium were used since previous studies had shown that this rate of inoculation was sufficient to induce suppression in media amended with mature composted hardwood bark.

Bacterial isolates were grown for 3–4 days in 50 ml. flasks of nutrient broth on a rotary shaker. The resultant cells were separated from the culture medium by centrifugation and resuspended in a phosphate buffer, pH 6.7. The bacteria were added to the container media at a concentration of $10^5$–$10^6$ cells per gram dry weight container medium.

The compost-amended container medium used in these experiments were either heated to 60° C. for 5 days in a forced air oven or prepared with compost removed from the hot center (temperature 50°–60° C.) of a compost pile. The media used were thus devoid of mesophilic microorganisms and therefore conducive. Disease severity levels obtained in media with added potential antagonists were compared with those in either heated media or media amended with center compost without added potential antagonists.

The only fungal antagonists found to suppress both Rhizoctonia and Pythium were species of *Trichoderma hamatum* and *T. harzianium*, especially the aforementioned *T. hamatum* isolate 382. A.T.C.C. No. 20765 and isolate 559, A.T.C.C. No. 20764. One isolate of *penicillium funiculosum* also significantly reduced Pythium disease severity. No effective actinomycete antagonists with activity against both diseases were isolated.

Only two bacterial isolates showed good activity against both diseases, namely the aforementioned *Xanthomonas maltophilia (Pseudomonas maltophilia)* isolate 76, A.T.C.C. No. 53199 and Flavobacterium isolate 299, A.T.C.C. No. 53198.

To evaluate the ability of these antagonistic microorganisms to induce suppression of Rhizoctonia and Pythium damping-off in a variety of media, further experiments were conducted in which the *T. hamatum* isolate 382, the *Xanthomonas maltophilia (Pseudomonas maltophilia)* isolate 76 and the *Flavobacterium balustinum* isolate 299 were added singly or in combination to composted sewage sludge, composted hardwood bark and past media. The composted hardwood bark had been cured for 16 weeks to allow development of maximum activity of Trichoderma antagonists. The composted hardwood bark was removed from the center of a windrow in which the temperature at the time of collection ranged from 55°–60° C. The composted sewage sludge had been cured for 12 weeks after screening and the samples used were removed from the center of a windrow, the temperature at this central area being from 43° to 49° C. Both windrows had been turned every two weeks throughout curing.

The Trichoderma was cultured on potato-dextrose agar for two weeks. Spores were scraped off plates, suspended in water and added to the medium at an inoculation rate of $10^4$ colony forming units per gram dry weight of medium. The two bacterial isolates were cultured in nutrient broth for 96 hours at 24° C. and added to the media at an inoculation rate of $10^6$ colony forming units per gram dry weight of medium.

All the inoculated media were incubated at 24° C. in polyethylene bags at a moisture level of 30–38 weight percent. After one day, and 1, 2, 4 and 8 weeks of incubation, samples of the amended media were assayed for suppressiveness to Rhizoctonia and Pythium damping-off by growing radishes and cucumbers respectively in the media.

Figure 1:
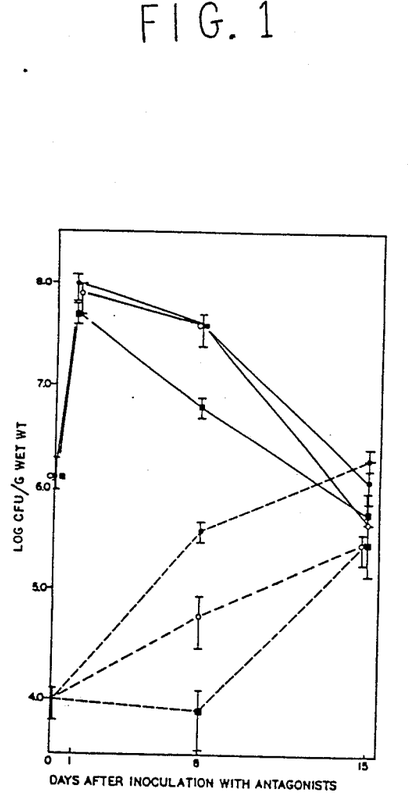
FIG. 1 is a chart of the population development of *F. balustinum* 299R and *T. hamatum* 382 in a container medium amended with compost and planted with cucumber.

FIGS. 1–3 of the drawings in my patent No. 4,642,131 show the results obtained with peat, composted hardwood bark and composted sewage sludge-amended media inoculated with Rhizoctonia while FIGS. 4–6 show the results obtained using the same media and Pythium inoculants. In each Figure, disease severity levels are given for the uninoculated medium (designated "check"), the pathogen-inoculated medium receiving no inoculation of the antagonistic microorganism (designated "inoc.") and for the *T. hamatum* isolate 382, the *Xanthamonas maltophilia (Pseudomonas maltophilia)* isolate 76, the *Flavobacterium balustinum* 299, and the combinations of isolates 382 and 76, and 383 and 299. In the FIGS. 1–4, the LSD (at the 95% confidence level) is 0.36, while in FIGS. 4–6 the same parameter is 0.84.

The FIGS. in 1–3 showing the results for Rhizoctonia damping-off show that disease incidence was highest in the bags assayed one day after inoculation. The incidence of disease diminished with incubation time in all the media. However, disease severity levels decreased more rapidly and reached lower levels in composted hardwood bark and composted sewage sludge-amended media than in composted peat amended media. In all cases other than the uninoculated media, disease severity levels in composted peat amended media were significantly higher than in the corresponding composted hardwood bark and composted hardwood bark and composted sewage sludge amended media. Except for two exceptions noted in the following sentence, the disease severity levels observed in composted sewage sludge and composted hardwood bark amended media were not significantly different from one another. The two exceptions were the disease levels in composted hardwood bark amended media inoculated with *T. hamatum* 382, which was significantly lower than those in the corresponding composted sewage sludge amended medium and the disease levels in the composted municipal sludge inoculated with the *Xanthmonas maltophilia (Pseudomonas maltophilia)*, which was significantly lower than those in the corresponding composted hardwood bark amended medium.

The reduction in disease severity levels with incubation time in both composted hardwood bark and composted sewage sludge amended media without the addition of antagonists suggests that natural colonization of the media was sufficient to produce significant disease suppression. However, the addition of antagonists to these batches of media had a significant affect in reducing disease severity in some cases. For example, the addition of *T. hamatum* 382 to composted hardwood bark medium did result in significantly lower disease severity levels in comparison with the same medium which did not receive the *T. hamatum*. No corresponding effect of the addition of *T. hamatum* alone was observed in composted sewage sludge amended medium.

The addition of *T. hamatum* 382, either alone or in conjunction with *Flavobacterium balustinum* 299 to peat medium significantly lowered disease severity levels but these levels still remained significantly higher than those observed in the composted hardwood bark and composted sewage sludge amended media, thus indicating that the peat medium not amended with either type of compost remained conducive.

The data presented in FIGS. 4-6 of the drawings in my Pat. No. 4,642,131 relating to suppression of damping-off caused by *P. ultimum* show many of the same tendencies as in the Rhizocotonia assays shown in the FIGS. 1-3. In general, the levels of disease severity in the composted sewage sludge and composted hardwood bark-amended media were lower than those in the peat medium. Except for the composted sewage sludge that was not inoculated with antagonistic microorganisms, the levels of disease were significantly lower in every composted hardwood bark and every composted sewage sludge amended medium as compared with the corresponding peat medium. Furthermore, the disease severity levels in the composted hardwood bark amended media to which antagonists were added were not significantly different from one another.

As in the case of the Rhizoctonia assays, the disease severity in the Pythium assays declined with time in the composted hardwood bark amended media both with and without the addition of antagonists. Thus, natural colonization of the composted hardwood bark amended medium appeared to be sufficient to induce significant disease suppression. Disease levels in some composted hardwood bark amended media inoculated with antagonistic microorganisms were, after 8 weeks of incubation, not significantly different from their uninoculated counterparts, suggesting that the composted hardwood bark amended medium had, in this case, become naturally strongly suppressive. In contrast, in the sewage sludge amended medium, the results shown in the FIGS. 4-6 indicate that natural colonization by antagonistic microorganisms either did not occur or was insufficient to result in Pythium suppression. This has also been observed in industry under commercial conditions for *R. solani*. In the composted sewage sludge amended medium without added antagonistic microorganisms, the Rhizoctonia disease levels experienced were not significantly different from those in the corresponding peat medium. However, as is shown in Example 3, the addition of antagonistic microorganisms to the composted sewage sludge amended medium did significantly reduce the levels of disease severity.

Disease levels in composted sewage sludge amended media with added antagonistic microorganisms were, in all cases, significantly lower than the corresponding disease levels in peat medium. In addition, the composted sewage sludge amended medium inoculated with either *Xanthomonas maltophilia Pseudomonas maltophilia* 76 or the combination of *T.hanatum* 382 and *Flavobacterium balustinum* 299 displayed significantly lower disease severity levels, as compared to the same medium without the added antagonistic microorganisms.

From the foregoing results, it appears that composted hardwood bark and composted sewage sludge amended media can become suppressive to Rhizoctonia and Pythium within 4 to 8 weeks of incubation; in contrast peat media remained conducive. In the particular batch of composted hardwood bark used in these experiments, natural colonization was sufficient to result in disease suppression and the addition of antagonists had little effect in increasing levels of suppression for both pathogens. On the other hand, in the composted sewage sludge amended medium, natural colonization was found to be sufficient to induce suppression of Rhizoctonia but not Pythium. Addition of the antagonistic microorganisms to this batch of composted sewage sludge in accordance with the invention did successfully induce suppression of Pythium. Furthermore, as noted above, the development of suppressiveness in compost media not amended with antagonistic microorganisms is highly variable and unpredictable. These experiments therefore indicated that adding antagonistic microorganisms to compost after peak heating provides a practicable method of inducing predictable levels of suppressiveness to both Rhizoctonia and Pythium.

Further experiments with composted hardwood bark indicated that the combinations of *T. hamatum* 382 or 559 in combination with Flavobacterium 299 were effective in inducing suppression not only to Rhizoctonia and Pythium but also to wilt caused by *Fusarium oxysporum* f. sp. conglutinans race 2 (Plant Dis. 70: 1023-1027 (1986)).

EXAMPLE 3

This example illustrates container media amended with sludge and bark composts, of which various amended media were and were not, inoculated with *Trichoderma hamatum* and various bacterial antagonists to evaluate suppression of Rhizoctonia and Pythium damping-off.

Compost and container media. A container medium containing sludge compost medium (CMS) was prepared with CMS, Canadian sphagnum peat and perlite (1:2:1, v/v, pH 5.5). CMS was composted municipal sludge obtained from the Southwesterly Composting Facility, Columbus, Ohio. It was prepared from polymer-dewatered, aerobically digested municipal sewage sludge using the static aerated pile composting process (Epstein et al., Journal WPCF 48: 688-694, 1976; Finstein et al., Bio/Technology 1: 347-353, 1983). After a minimum of two 21 day periods of composting in aerated piles, compost was screened to remove wood chip particles $>1.8$ cm diameter. Thereafter, it was cured in windrows of various heights (up to 6 m high) for up to one year prior to utilization. Temperatures $>70°$ C. may occur in such high curing piles (Kuter et al., 1975). This prepared medium was not amended with fertilizer since sludge compost media release adequate amounts of plant nutrients for at least 6 weeks after potting (Chaney et al., J. Am. HortSci. 105: 485-492, 1980).

A bark compost medium was prepared as follows. Fresh hammermilled (all particles $>1.0$ cm diameter) hardwood tree bark (mostly Quercus spp.), obtained from a commercial source in South Charleston, Ohio, was amended with 2 kg ammonium nitrate and 1.5 kg urea/$m^3$ bark. Water was added to adjust the moisture level to 55% on a dry weight basis. Compost was prepared in 25 $m^3$ piles (2 m high) that were turned biweekly. Water was added as needed to maintain a moisture level of approximately 55% (on a dry weight basis). Temperatures in the center of the compost pile were monitored routinely. After 4 months composting, bark compost was mixed with Canadian sphagnum peat and perlite (5:2:3 v/v, pH 6.0). This bark compost medium was amended with 10 gm of a commercially available 14-14-14 slow release fertilizer per liter. The sludge compost medium was not amended with fertilizer because it releases adequate levels of macro nutrients for several weeks (Chanely et al., 1980 supra). The perlite added to the bark and sludge compost media served to adjust the air-filled pore space at container moisture capacity (10 cm tall column) to 15-20% (calculated from soil moisture desorption curves).

Several types of these bark compost (CHB) and sludge compost (CMS) media, either conducive or suppressive to Rhizoctonia and Pythium damping-off were prepared. Naturally suppressive sludge and bark compost media were prepared with samples removed from the low temperature edge of compost piles (>4 month-old) and are referred to hereafter as $CMS_e$ and $CHB_e$ media, respectively. Naturally conducive media ($CHB_c$ or $CMS_c$) were prepared with samples removed from the high temperature center (>60° C. for 5 consecutive days before samples were taken) of compost piles. Because compost piles with center temperatures of >60 C. were not always available, conducive media were also prepared by heat treatment (5 days, 60 C.) or $CHB_c$ or $CMS_c$ media samples in polyethylene bags in an oven (Nelson and Hoitink, Phytopathology 73: 274–278, 1983). For this treatment, control $CHB_e$ or $CMS_e$ samples were stored 4 weeks at 25 C. This to insure that they were naturally suppressive to both diseases. These conducive and suppressive media are referred to hereafter as $CHB_{60}$ or $CMS_{60}$ and $CHB_{25}$ or $CMS_{25}$, respectively. For some experiments, a CHB medium was autoclaved 1 hour in 2 l bags on two consecutive days to destroy the entire microflora and thus render them totally conducive to disease development.

Bioassays to detect suppression of Pythium and Rhizoctonia damping-off. Suppression of Pythium damping-off was determined with a cucumber bioassay. Isolate 211 of *Pythium ultimum* Trow, originally isolated from a diseased poinsettia plant at The Ohio State University, Columbus, Ohio was used throughout this example. Inoculum was prepared in a chopped potato soil medium that contained 50 grams chopped potato and 500 ml soil in a 1-L flask (Ko and Hora, 1971). It was sterilized for 1 hour on two consecutive days, and seeded with two 5-mm-diameteragar disks from a 24 hour culture of *P. ultimum* on lima bean agar (LBA, 10 g frozen lima bean, 20 g Difco agar/L distilled water). The chopped potato soil medium was incubated 14 days at 25 C., removed from the flask, air dried overnight, ground with a mortar and pestle sieved through a 2-mm mesh sieve and collected on a 1-mm mesh sieve. The 1- to 2-mm diameter particles were used as inoculum of *P. ultimum*.

Cucumber seeds (*Cucumis sativus* L., cultivar 'Straight Eight', 90% germination, eight per pot) were planted 1 cm deep in disposable styrofoam pots (10 cm deep, 10 cm top diameter) with a perforated base containing approximately 400 ml container medium. Unless specified otherwise, 1.5 g inoculum of Pythium was added per 2 L container medium in polyethylene bags. Bags were shaken vigorously to ensure uniform distribution of inoculum and contents were then distributed into five pots. Plants were grown at a constant temperature of 20 C. and under 16 hours illumination (225 $uE_M^{-2}$ sec$^{-1}$) per day and were watered daily. A disease severity rating was made 10 days after planting according to the following scale: 1=symptomless; 2=emerged, but diseased (either wilted, yellowed or with visible lesions on hypocotyl); 3=post and 4=pre-emergence damping-off. A mean of eight seedings in a pot was computed to represent one replication. Diseased seedlings and nongerminated seeds were surface sterilized in 1% sodium hypochlorite (30 sec), rinsed in sterile distilled water three times, and placed on a semiselective Pythium medium, SA-PBNC (Schmitthenner, A. F. 1980. Pythium species: Isolation, biology and identification. Pages 33–39 in: Advances in Turfgrass Pathology. P. O. Larsen and B. J. Joyner, eds. Proc of the Symposium on Turfgrass Diseases, May 15–17, 1980, Columbus, Ohio. Harcourt Brace Jovanovich, Inc., One East First Street, Duluth, MN 55802. 197 pp.), to reisolate the pathogen. The SA-PNBC medium contained the following ingredients per L distilled water: 2.5 g sucrose, 0.27 g asparagine, 0.15 g $KH_2PO_4$, 0.1 g $MgSO_7H_2O$, 80 mg $CaCl_2.2H_2O$, 2 mg thiamine HCl, 10 mg ascorbic acid, 27 mg Terraclor (75% pentachloronitrobenzene), 20 mg Benlate (50% benomyl), 100 mg nemycin sulfate, 10 mg chloromycetin, 1 ml $ZnSO_4.7H_2O$ (44 mg/10 ml water), 1 ml $FeSO_4.7H_2O$, (10 mg/10 ml water), 1 ml $MnCl_2.4H_2O$ (7 mg/100 ml water), 2 ml chloesterol (5 mg/ml N-N dimethyl foramide) and 20 g Difco agar. The ingredients were added and dissolved one at a time. Isolations also were made from seeds that had not germinated in uninfested container media.

Suppressiveness to Rhizoctonia damping-off was determined with a radish (*Raphanus sativus* L. cv. 'Early Scarlet Globe', 97% germination) biassay (Nelson and Hoitink, 1983). Soil inoculum of *Rhizoctonia solani* Kuhn was produced in Ko and Hora's chopped potato soil mixture, air dried and screened to yield 1-2 mm soil inoculum pieces as described above. Container media were infested with 0.5 g *R. solani* soil inoculum propagules/l (equivalent to approximately 2.5 g air dry inoculum/kg dry wt. container medium. Radish seeds were planted at a mean distance of 1.4 cm from each other in pots containing approximately 400 ml container medium (32 seeds/10 cm diameter pot). Pots were watered and incubated in a growth chamber at 25 C. under continuous illumination (22 uEM$^{-2}$ sec$^{-1}$). After 7 days, plants were rating according to a disease severity scale in which: 1=symptomless; 2=diseased but not damped-off; 3=post-emergence damping-off; and 4=pre-emergence damping-off (seedlings that did not emerge). Mean disease severity ratings were based on five replicates of 32 seeds/pot. Completely randomized designs were used in all bioassays. One way analysis of variance was performed using MINITAB computer program. Separations of means were based on least significant difference (LSD, P=0.05).

Uninfested media (checks) were included with each bioassay to ensure that samples tested did not contain pathogens and that disease was due to added inoculum. All bioassays, unless specified otherwise, were set up within 24 hours after samples were collected and media prepared. Diseased seedlings were routinely plated on acidified Difco PDA to verify presence of *R. solani*.

Isolation of antagonists. Bacteria were isolated by baiting with (1) radish roots and (2) cucumber roots (*Cucumis sativus* L. cv. 'Straight Eight'), and (3) with Rhizoctonia and Pythium soil inoculum propagules incubated in sandwiches in suppressive batches of bark and sludge compost media collected from various nurseries, using procedures described previously for isolation of fungal antagonists from the bark compost container medium (Nelson et al., Phytopathology 73: 274–278, 1983). After recovery from media, these baits were rinsed in sterile distilled water and next comminuted in a Ten Broeck homogenizer (0.3 ml distilled water). Suspensions thus prepared were diluted in buffer (7 g $K_2HPO_4$, 3 g $KH_2PO_4$ and 0.2 g $MgSO_4.7H_2O/l$) and plated on Difco nutrient agar (NA) and on King's B agar (KB). Plates were incubated 48 hours at 25 C. and colonies of candidate antagonists were picked at random and purified by streaking and dilution plating on the media from which the bacteria had been isolated originally. Pure culutres were stored at 4 C. on yeast dextrose calcium carbonate agar. Cultures were tested for antagonistic activity in bioassays, as described below. Effective bacterial antagonists were then stored at −70 C. in glycerol-water (Sleesman and Leban, Plant Dis. Rept. 62: 910–913, 1978).

Candidate bacterial antagonists were cultured 48 hours in Difco nutrient broth (NB) shake culutres (50 ml/250 ml flask, 25 C.), washed by centrifugation and resuspended into the dilution buffer described above to population levels of approximately $10^8$ CFU/ml (verified by dilution plating on NA). These cell suspensions were added to 2 l conducive $CHB_{60}$ and $CMS_{60}$ container media in polyethylene bags. The inoculum was then distributed evenly by shaking bags vigorously for 30 sec. The final candidate bacterial antagonist popoulation level was approximately $10^{6-7}$ CFU/g dry wt. container medium. Thereafter, Rhizoctonia or Pythium soil inoculum (0.5 g/L) was added, as described previously. Control treatments were not infested. The infested $CHB_{60}$ and $CMS_{60}$ container media were then distributed evenly in five pots and assayed for suppressiveness as described in the bioassay section. Control treatments were the conducive $CHB_{60}$ and $CMS_{60}$ media not treated with potential antagonists and the naturally suppressive $CHB_{25}$ and $CMS_{25}$ media, all infested with R. solani.

Trichoderma hamatum 382 (ATCC20765), originally isolated from bark compost (Nelson et al., 1983), was added at initial population levels of $10^4$ CFU/g dry weight of the conducive $CHB_{60}$ and $CMS_{60}$ container media. Additional Trichoderma and other fungal isolates were from sludge compost with a selective Trichoderma medium (Elad et al., 1981) and acidified PDA, respectively, and compared in efficacy with T. hamatum 382 in both Pythium and Rhizoctonia bioassays. Efficacy of antagonist treatments was compared by analyses of their mean disease severity indexes established in $CHB_{60}$ and $CMS_{60}$ bioassays. Naturally suppressive container media were included as control treatments.

Identification of bacterial antagonists. Bacteria were identified using standard methods and characteristics described by Kreig and Holt eds., Bergey's Manual of Systemic Bacteriology, 1st ed., Baltimore, MD, Williams and Wilkens (1984). Standard diagnostic media were prepared according to methods and formulae given by Fahy and Hayward (1983). Bacillus spp. and members of Enterobacteriaceae were identified using Gordon et al. (1973) and The Genus Bacillus. Agriculture Handbook No. 427. Agric. Res. Serv. USDA, Washington, DC. and Kelley, M. T., et al 1985. Enterobacteriaceae. Pages 263-276 in: Manual of Clinical Microbiology. 4th ed. E. H. Lennette, A. Balows, W. J. Hausler, and H. J. Shadomy, eds. Am. Soc. for Microbiology, Washington, DC 1149 pp., respectively. The taxonomic identity of the isolates was verified by analysis of their fatty acid profiles with an HP5898A microbial identification system using the aerobic library version 1.1, according to procedures specified by the manufacturer (Hewlett Packard, Avondale Div. Rt. 41, Avondale, PA 19311-0900).

Production of antifungal substances. The ability of the bacterial antagonists to produce antifungal substances against R. solani and T. hamatum was determined by paired in vitro assays on potato dextrose agar (PDA) and KB agar. Bacteria were streaked as a broad band on the agar and allowed to grow for 3 days before an agar plug of either R. solani or T. hamatum 382 was placed on the plate 40 mm away from the bacteria. Zones of inhibition were measured after 4 days at 25 C.

Isolation of mutants. To determine the distribution of selected antagonists in container media, spontaneous rifampicin resistant mutants of Pseudomonas putida 315, Flavobacterium balustinum 299 and Xanthomonas maltophilia 76 were isolated. Cultures of these three antagonists, incubated 24 hours in NB in a shaker at 25 C., were seeded ($10^9$ cells/plate) on KB agar (P. putida 315) or NA (F. balustinum 299 and X. maltophilia 76), both supplemented with 100 ug rifampicin/ml. After 48 hours at 25 C., colonies of spontaneous resistant mutants were streaked onto the same media, but without rifampicin. Single colony isolates were stored in 15% glycerol at −70 C. These cultures were then tested for stability of rifampicin resistance, growth rate and antagonistic activity in the bioassay. Strains not significantly different (P=0.05) in antagonistic activity (P. putida 315R, F. balustinum 299R and X. maltophilia 76R) from the wild types were selected.

Antagonist enumeration. Pseudomonas putida 315R was enumerated on a selective medium (Sands and Rovira, App. Microbiol. 20: 513-514, 1970) [KB agar supplemented with novobiocin (50 ug/ml), penicillin G (75 units/ml), cycloheximide (80 ug/ml)], to which rifampicin (100 ug/ml) was added. F. balustinum 299R and X. maltophilia 76R were enumerated on NA supplemented with crystal violet (1.5 ug/ml), neomycin (40 ug/ml), cycloheximide (80 ug/ml), and rifampicin (100 ug/ml). Container media not infested with mutants were included as controls to check for (1) the occurrence of spontaneous rifampicin resistant mutants with identical colony types and (2) contamination among treatments. T. hamatum 382 was enumerated on Elad's medium (Elad et al., Phytoparasictico 9: 59-67, 1981).

Movement of antagonists from seeds into the rhizosphere and non-rhizosphere. Rifampicin resistant mutants were grown 24 hours in NB. Cells were collected by centrifugation and then resuspended in 10 ml phosphate buffer. Cucumber seeds were soaked 10 min in one of the bacterial suspensions and then planted in the conducive autoclaved CHB and $CHB_{60}$ media or the naturally suppressive $CHB_{25}$ container medium in styrofoam pots (9.5×17 cm, 14 cm "soil column"). Non-irrigated pots were sealed in individual polyethylene bags, and the others were irrigated daily. Six days after planting, pots were cut open and cucumber seedlings were carefully removed from the container medium. Particles of the container media were removed from tap roots. In addition, lateral roots were cut off because final population levels were based on root length (cm). The tap root was then cut into five 2-cm segments. Each segment was ground in 1 ml diluent (0.4M NaCl and 0.05M $MgSO_4$) with a mortar and pestle. Mutant populations were then enumerated by 10-fold serial dilutions (triplicate series) on the selective media. Three plants were used per treatment and each plant was considered as a replicate. The entire experiment was repeated once.

A separate set of pots was used to determine colonization of non-rhizosphere container media ("bulk soil") by bacterial antagonists. After the plant had been removed, 10 g container medium samples were taken from the top, middle and bottom of the pot. The samples were shaken in 50 ml diluent for 15 min and mutants were enumerated on selective media as described above. The experiment was performed twice.

Survival of antagonists in container media. *F. balustinum* 299R, *P. putida* 315R, and *X. maltophilia* 76R were added to the conducive autoclaved CHB and CHB$_{60}$ media and to the naturally suppressive CHB$_{25}$ medium at 10$^6$ CFU/g dry weight container medium. *T. hamatum* 382 was added at 10$^4$ CFU/g dry weight. One cucumber seed was planted in each pot. Pots were watered daily. Samples were taken at 0, 24 hours and at 7 day intervals thereafter, for a period of 28 days. All roots were carefully removed from container media. The medium from one pot was then shaken vigorously (30 sec) in a polyethylene bag (three replications/treatment) and mutant population levels in 10 g samples were then determined as described above. The experiment was repeated once.

In two other experiments survival of antagonists was evaluated in the naturally suppressive CHB$_e$ and the conducive CHB$_c$ container media. Efficacy of the antagonist treatments in suppression of Rhizoctonia damping-off in these container media was evaluated as well.

Efficacy of antagonists. A total of 652 bacterial isolates obtained by dilution plating from cucumber roots, radish roots and from Rhizoctonia or Pythium soil inoculum propagules, retrieved from naturally suppressive sludge compost and bark compost media were screened for their ability to induce suppression to Pythium and Rhizoctonia damping-off in the conducive CMS$_{60}$ and CHB$_{60}$ bioassays. Thirty fungal isolates and 90 bacterial isolates from sludge compost media were screened for efficacy in both bark and sludge compost media against Pythium and Rhizoctonia damping-off. Activity of these isolates in these two media did not differ consistently. The most efficacious Trichoderma isolate recovered from sludge compost media was an isolate of *Trichoderma pseudokoningii* Rifai. However, the disease severity level induced by this isolate against Rhizoctonia damping-off was not as high as that induced by *T. hamatum* 382 selected from among 277 Trichoderma strains originally isolated from bark compost (Nelson et al., Phytopathology 73: 1457–1462, 1983). *T. hamatum* 382, therefore, ws used in further work. Several *Pseudomonas putida* isolates, recovered among 90 bacterial isolates purified from sludge compost media, induced high levels of suppression to Phythium damping-off in both sludge and bark compost media. These isolates, therefore were evaluated in further studies.

The most efficacious isolates against Rhizoctonia damping-off in the sludge and bark compost media are listed in Tables 9 and 10 respectively. The taxonomic identity of the strains, with exception of *F. balustinum* 299, was verified by analysis of their fatty acid profiles.

Efficacy of bacterial antagonists as single treatments as compared to their efficacy if used in combination with *T. hamatum* 382 in the conducive sludge compost medium (CMS$_{60}$) not treated with antagonists was 2.9. Addition of *T. hamatum* by itself reduced the disease severity rating to 2.6. Addition of *T. hamatum* by itself reduced the disease severity rating to 2.6, which was not a significant difference (LSD$_{0.05}$=0.4). Several of the bacterial antagonists, i.e., *P. fluorescens* Al, *P. putida* strains 305, 315 and 371 as well as *P. stutzeri* 280, significantly reduced disease severity levels over that in the control. Most of the bacterial antagonists listed in Table 9 were significantly more effective if combined with *T. hamatum* 382.

The Rhizoctonia disease severity rating in the conducive bark compost medium (CHB$_{60}$) not treated with antagonists was 3.3 (Table 10).

TABLE 9

Suppression of Rhizoctonia damping-off induced by bacterial antagonists alone and in combination with *Trichoderma hamatum* in a sludge compost container medium

| Bacterial antagonist[1] | Disease severity rating[2] | |
|---|---|---|
| | Bacterial antagonist alone | Bacterial antagonist with *T. hamatum* |
| None | 2.9 | 2.6 |
| *Bacillus cereus* 106 | 3.0 | 2.0 |
| *Enterobacter cloacae* 127 | 2.6 | 2.6 |
| *E. cloacae* 313 | 2.1 | 2.1 |
| *Flavobacterium balustinum* 299 (ATCC53198) | 3.1 | 2.1 |
| *Janthinobacterium lividum* 275 | 2.7 | 2.5 |
| *Pseudomonas fluorescens* biovar III, A91 | 2.9 | 2.4 |
| *P. fluorescens* biovar V, A1 | 2.4 | 2.6 |
| *P. fluorescens* biovar V, A498 (ATCC53916) | 2.7 | 2.3 |
| *P. putida* 305 | 2.2 | 1.8 |
| *P. putida* 315 (ATCC 53915) 2.3 | 2.1 | |
| *P. putida* 371 | 2.3 | 2.5 |
| *P. stutzeri* 280 (ATCC53917) | 2.4 | 2.1 |
| *Xanthomonas maltophilia* 76 (ATCC53199) | 3.0 | 2.4 |
| LSD | 0.05 | 0.4 |

[1] Bacterial antagonists were added to the heated (60 C., 5 days) sludge compost container medium at initial population levels of 10$^6$ CFU/g dry wt. *T. hamatum* was added at 10$^4$ CFU/g dry wt.
[2] Inoculated with 0.5 g *Rhizoctonia solani* soil inoculum/l container medium. Mean disease severity rating determined 7 days after incubation at 26 C. from five pots plantad with 32 radish seeds each: 1-symptomless; 2-diseased but not damped-off; 3-post-emergence damping-off; and 4-pre-emergence damping-off. Mean disease severity in the container medium not infested with *R. solani* was 1.2.

TABLE 10

Suppression of Rhizoctonia damping-off induced by bacterial antagonists alone and in combination with *Trichoderma hamatum* in a bark compost container medium

| Bacterial antagonist[1] | Disease severity rating[2] | |
|---|---|---|
| | Bacterial antagonist alone | Bacterial antagonist with *T. hamatum* |
| None | 3.3 | 2.8 |
| *Bacillus cereus* 106 | 2.7 | 2.6 |
| *Enterobacter cloacae* 127 | 2.8 | 2.5 |
| *E. cloacae* 313 | 2.7 | 2.3 |
| *Flavobacterium balustinum* 299 (ATCC53198) | 2.4 | 2.1 |
| *Janthinobacterium lividum* 275 | 2.9 | 2.5 |
| *Pseudomonas fluorescens* biovar III A91 | 2.6 | 2.5 |
| *P. fluorescens* biovar V A1 | 3.0 | 2.4 |
| *P. fluorescens* biovar V A498 (ATCC53916) | 3.2 | 2.7 |
| *P. putida* 305 | 2.8 | 2.5 |
| *P. putida* 315 (ATCC53915) | 3.1 | 2.6 |
| *P. putida* 371 | 2.2 | 2.3 |
| *P. stutzeri* 280 (ATCC53917) | 2.5 | 2.1 |
| *Xanthomonas maltophilia* 76 (ATCC53199) | 2.4 | 2.5 |
| LSD | 0.05 | 0.3 |

[1] Bacterial antagonists were added to the heated (60 C., 5 days) bark compost container medium at initial population levels of 10$^6$ CFU/g dry wt. *T. hamatum* was added at 10$^4$ CFU/g dry wt.
[2] Inoculated with 0.5 g *Rhizoctonia solani* soil inoculum/l container medium. Mean disease severity rating determined 7 days after incubation at 26 C. from five pots plantad with 32 radish seeds each: 1-symptomless; 2-diseased but not damped-off; 3-post-emergence damping-off; and 4-pre-emergence damping-off. Mean disease severity in the container medium not infested with *R. solani* was 1.2.

Ten of 13 bacterial strains significantly (P=0.05) reduced damping-off when added as single antagonist treatments. *T. hamatum* 382, as a single antagonist treatment, reduced disease to a severity rating of 2.8. Its effect was significant (P=0.05) in this bark compost medium. Six of the bacterial strains listed (*E. cloacae* 313, *J. lividum* 275, *P. fluorescens* biovar V A1 and A498, *P. putida* 315 and *P. stutzeri* 280), when combined with *T. hamatum* 382, significantly (P=0.05) reduced the disease severity over that induced by the bacteria alone. Five bacterial strains (*E. cloacae* 313, *F. balustinum* 299, *P. fluorescens* biovar V A1, *P. putida* 371 and *P. stutzeri* 280), significantly (P=0.05) enhanced efficacy of *T. hamatum* 382 used by itself. Three bacterial strains, i.e., *P. fluorescens* A1 and A498 and *P. putida* 315 had a significant effect only if added in combination with *T. hamatum* 382. Interestingly, none of the bacterial antagonists reduced efficacy of the *T. hamatum* 382 treatment, suggesting that there was no antagonism among these bacterial strains and the Trichoderma isolate even though *R. solani*, also a fungus, was controlled.

In several of the bioassays, whether in the sludge compost or the bark compost medium, single antagonist treatments varied in efficacy. An example of this variability is the efficacy of *F. balustinum* 299 in the bark compost assay in Table 10 and lack of its efficacy in Table 9 in the sludge compost medium. This is not a "single experiment observation." If combined with *T. hamatum* 382, however, this treatment was consistently effective (mean disease severity ratings of 2.1 in both bioassays).

Efficacy of the antagonist treatments for suppression of Pythium damping-off in the sludge compost medium is presented in Table 11. The disease severity rating in the conducive $CMS_{60}$ medium was 3.4 (no antagonists were added in this treatment). Many of the bacterial isolates, when applied as single treatments, effectively suppressed Pythium damping-off. Others, i.e. *F. balustinum* 299 and *P. putida* 305 were not effective in this bioassay.

TABLE 11

Suppression of Pythium damping-off induced by bacterial antagonists alone and in combination with Trichoderma hamatum in a sludge compost container medium

| | Disease severity rating[2] | |
|---|---|---|
| Bacterial antagonist[1] | Bacterial antagonist alone | Bacterial antagonist with *T. hamatum* |
| None | 3.4 | 2.3 |
| *Bacillus cereus* 106 | 1.6 | 2.6 |
| *Enterobacter cloacae* 127 | 1.5 | 1.5 |
| *E. cloacae* 313 | 1.5 | 1.4 |
| *Flavobacterium balustinum* 299 (ATCC53198) | 3.3 | 1.1 |
| *Janthinobacterium lividum* 275 | 1.9 | 1.3 |
| *Pseudomonas fluorescens* biovar IV, A91 | 2.5 | 1.2 |
| *P. fluorescens* biovar V. A1 | 1.5 | 2.1 |
| *P. fluorescens* biovar V, A498 (ATCC53916) | 1.7 | 1.1 |
| *P. putida* 305 | 3.1 | 1.6 |
| *P. putida* 315 (ATCC53915) | 2.3 | 1.7 |

TABLE 11-continued

Suppression of Pythium damping-off induced by bacterial antagonists alone and in combination with Trichoderma hamatum in a sludge compost container medium

| | Disease severity rating[2] | |
|---|---|---|
| Bacterial antagonist[1] | Bacterial antagonist alone | Bacterial antagonist with *T. hamatum* |
| *P. putida* 371 | 1.3 | 1.7 |
| *P. stutzeri* 280 (ATCC53917) | 1.4 | 1.6 |
| *Xanthomonas maltophilia* 76 (ATCC53199) | 1.6 | 2.7 |
| LSD | 0.05 | 0.8 |

[1]Bacterial antagonists were added to the heated (60 C., 5 days) sludge compost container medium at initial population levels of $10^6$ CFU/g dry wt. *T. hamatum* was added at $10^4$ CFU/g dry wt.
[2]Inoculated with 0.5 g *Pythium ultimum* soil inoculum/l container medium. Mean disease severity rating determined 7 days after incubation at 26 C. from five pots planted with eight cucumber seeds each: 1-symptomless; 2-diseased but not damped-off; 3-post-emergence damping-off; and 4-pre-emergence damping.off. Mean disease severity in the container medium not infested with *P. ultimum* was 1.3.

*T. hamatum* 382 by itself had a significant (P=0.05) effect on Pythium damping-off in this assay. However, all combination treatments with the exception of *X. maltophilia* 76 were highly effective (P=0.01). Trends, therefore, were similar to those found for Rhizoctonia damping-off.

Effects of the antagonists against Phythium damping-off in the bark compost medium were determined and are presented in Table 12. Results were similar to those presented here for sludge compost in Table 11.

Efficacy of *T. hamatum* 382 and of *F. balustinum* 299R in container media amended with naturally suppressive composts from the edge and in media amended with compost from the center of piles ($CHB_e$ and $CHB_c$ and $CMS_e$ and $CMS_c$) was followed in two experiments. Results in the bark and sludge compost media were similar. Mean disease severity values for both the suppressive edge compost and the conducive high temperature center compost media not infested with *R. solani* were 1.3. Values in *R. solani*-infested edge and center container media were 2.7 and 3.7, respectively. Mean disease severity values for the *T. hamatum* 382 treatment, the *F. balustinum* 299R treatment and the combination treatment of these antagonists in center high temperature compost media were 3.0, 3.5 and 2.5, respectively ($LSD_{0.05}=0.4$). The combination antagonist treatment, therefore, again was significantly (P=0.05) more effective than the single antagonist treatment. The treatments had no effect in edge compost media that already were suppressive.

Production of antifungal substances. Of 13 bacterial strains, only four produced antifungal substances against *R. solani* in paired in vitro assays. Two fluorescent pseudomonads (A1 and A91) produced inhibition zones on both PDA and KB agar. *E. cloacae* 313 inhibition zones on PDA only, whereas *X. maltophilia* 76 produced inhibition zones on KB agar only (Table 13).

TABLE 12

Effect of antagonists on suppression of Pythium damping-off of cucumber in container media amended with composted hardwood bark (CHB) or composted municipal sludge (CMS)

| Compost sample[a] | Antagonist inoculum[b] | Pythium inoculum[c] | Disease severity[d] | |
|---|---|---|---|---|
| | | | CHB | CMS |
| Edge | — | — | 1.2 | 1.1 |
| Edge | — | + | 1.5 | 1.8 |
| Center | — | — | 1.1 | 1.2 |
| Center | — | + | 3.0 | 2.9 |
| Center | *Trichoderma hamatum* #382 | + | 1.8 | 2.4 |

TABLE 12-continued

Effect of antagonists on suppression of Pythium damping-off of cucumber in container media amended with composted hardwood bark (CHB) or composted municipal sludge (CMS)

| Compost sample[a] | Antagonist inoculum[b] | Pythium inoculum[c] | Disease severity[d] CHB | CMS |
|---|---|---|---|---|
| Center | Flavobacterium balustinum #299 | + | 1.5 | 1.7 |
| Center | Xanthomonas maltophilia #76 | + | 1.9 | 2.0 |
| Center | 10% (v/v) edge compost | + | 1.7 | 2.1 |
| LSD (P = 0.05) | | | 0.6 | 0.7 |

[a]Compost samples taken from the edge (35 C) or center (60 C) of compost piles, respectively, and incorporated into container media.
[b]Initial inoculum levels were $10^5$ and $10^7$ cfu/g dry wt for fungi and bacteria, respectively.
[c]Container media infested with 0.75 g Pythium inoculum/L (+) or non-infested (−).
[d]Disease severity rating 10 days after planting, 1 = healthy, 2 = emerged but diseased seedlings; 3 = post- and 4 = pre-emergence damping-off. Data were means of 40 seedlings in five replicates.

Only three bacterial strains produced zones of inhibition against *T. hamatum* 382. Two of these, *E. cloacae* 313 and *P. fluorescens* biovar III A91, produced inhibition zones on PDA only, while the third one, *P. stutzeri* 280 produced inhibition zones on KB agar only.

Colonization of cucumber roots by bacterial antagonists. The ability of *F. balustinum* 299R, *P. putida* 315R and *X. maltophilia* 76R to colonize cucumber roots in conducive autoclaved CHB and CHB$_{60}$ media and in the suppressive CHB$_{25}$ container media is presented in Table 14. In the autoclaved container medium, all three mutants consistently colonized the entire cucumber root system from the treated seed, irrespective of irrigation treatment. Furthermore, highest population levels were established on root tips in irrigated pots in this medium. In the conducive CHB$_{60}$ container medium, root colonization was less extensive and in non-irrigated pots, population levels on root tips were low. Irrigation, again, increased population levels on root tips. Finally, in the suppressive CHB$_{25}$ container medium, only the 4 cm root area nearest the seed was colonized. Irrigation did not result in colonization of root tips by the mutants.

Colonization of container media by bacterial antagonists. *F. balustinum* 299R and *X. maltophilia* 76R did not establish high population levels at a distance greater than 2 cm from the infested seed in media that were not irrigated (Table 15). Without irrigation, *P. putida* 315R also did not colonize the CHB$_{60}$ or the CHB$_{25}$ medium, but it did establish high population levels in the autoclaved CHB medium, up to a distance of 6-8 cm from the treated seed.

All three mutants established highest population levels thoughout the irrigated, autoclaved container medium.

TABLE 13

Production of antifungal substances by bacterial antagonists against Rhizcotonia solani and Trichoderma hamatum on potato dextrose agar (PDA) and King's B agar (KB)

| Bacterial antagonist | Rhizoctonia solani PDA | KB | Trichoderma hamatum PDA | KB |
|---|---|---|---|---|
| *Bacillus cereus* 106 | −1 | — | — | — |
| *Enterobacter cloacae* 127 | — | — | — | — |
| *E. cloacae* 313 | +++ | — | ++ | — |
| *Flavobacterium balustinum* 299 (ATCC53198) | — | — | — | — |
| *Janthinobacterium lividum* 275 | — | — | — | — |
| *Pseudomonas fluorescens* biovar III A91 | + | +++ | + | — |
| *P. fluorescens* biovar V A1 | + | + | — | — |
| *P. fluorescens* biovar V A498 (ATCC53916) | — | — | — | — |
| *P. putida* 305 | — | — | — | — |
| *P. putida* 315 (ATCC53915) | — | — | — | — |
| *P. putida* 371 | — | — | — | — |
| *P. stutzeri* 280 (ATCC53917) | — | — | — | ++ |
| *Xanthomonas maltophilia* 76 (ATCC53199) | — | ++ | — | — |

[1]−, +, ++ and +++ represent 0, 5, 10, and 15 mm wide zones of inhibition in paired petri dish assays.

TABLE 14

Colonization of cucumber roots by bacterial antagonists introduced with inoculated seeds in a container medium pre-treated with various temperature regimes

| Distance from seed (cm) | Log CFU/cm root[1] Autoclaved Not irrigated | Irrigated | Heated (60 C, 5 days) Not irrigated | Irrigated | Control (25 C) Not irrigated | Irrigated |
|---|---|---|---|---|---|---|
| (a) *Flavobacterium balustinum* 299R | | | | | | |
| 0-2 | 6.98 ± 0.05 | 6.89 ± 0.18 | 5.98 ± 0.16 | 5.63 ± 0.16 | 5.64 ± 0.04 | 4.32 ± 0.16 |
| 2-4 | 5.83 ± 0.19 | 6.15 ± 0.23 | 3.44 ± 0.52 | 5.20 ± 0.47 | 3.12 ± 0.21 | 2.55 ± 0.58 |
| 4-6 | 4.56 ± 0.28 | 5.97 ± 0.27 | 2.70 ± 0.68 | 4.12 ± 0.33 | 2.33 ± 0.21 | ND |
| 6-8 | 4.31 ± 0.57 | 5.87 ± 0.20 | 2.46 ± 0.59 | 3.89 ± 0.24 | ND[2] | ND |
| 8-10 | 4.43 ± 0.03 | 5.70 ± 0.15 | 1.88 ± 0.48 | 4.15 ± 0.39 | ND | ND |
| (b) *Pseudomonas putida* 315R | | | | | | |
| 0-2 | 6.49 ± 0.02 | 6.42 ± 0.09 | 5.07 ± 0.34 | 6.30 ± 0.16 | 4.70 ± 0.28 | 3.36 ± 0.49 |
| 2-4 | 5.82 ± 0.17 | 5.56 ± 0.12 | 3.30 ± 0.23 | 4.08 ± 0.58 | 2.79 ± 0.80 | 2.07 ± 0.34 |
| 4-6 | 5.37 ± 0.13 | 5.36 ± 0.13 | 3.38 ± 0.18 | 3.78 ± 0.36 | 2.20 ± 0.80 | 1.77 ± 0.20 |
| 6-8 | 4.61 ± 0.18 | 5.32 ± 0.06 | 2.72 ± 0.31 | 3.92 ± 0.74 | 1.86 ± 0.46 | ND |
| 8-10 | 3.70 ± 0.14 | 5.33 ± 0.17 | 2.13 ± 0.50 | 3.77 ± 0.47 | ND | ND |
| (c) *Xanthomonas maltophilia* 76R | | | | | | |
| 0-2 | 5.84 ± 0.56 | 6.97 ± 0.08 | 4.74 ± 0.29 | 6.47 ± 0.14 | 3.85 ± 0.62 | 4.30 ± 0.30 |
| 2-4 | 3.63 ± 0.65 | 6.16 ± 0.10 | 2.96 ± 0.44 | 5.00 ± 0.23 | 2.08 ± 0.31 | 3.38 ± 0.52 |
| 4-6 | 3.22 ± 0.91 | 6.00 ± 0.06 | 2.22 ± 0.45 | 4.60 ± 0.29 | ND | 2.09 ± 0.35 |
| 6-8 | 1.58 ± 0.36 | 5.84 ± 0.08 | 1.79 ± 0.23 | 4.20 ± 0.36 | ND | 1.86 ± 0.32 |

TABLE 14-continued

Colonization of cucumber roots by bacterial antagonists introduced with inoculated seeds in a container medium pre-treated with various temperature regimes

| | Log CFU/cm root[1] | | | | | |
|---|---|---|---|---|---|---|
| Distance | Autoclaved | | Heated (60 C, 5 days) | | Control (25 C) | |
| from seed (cm) | Not irrigated | Irrigated | Not irrigated | Irrigated | Not irrigated | Irrigated |
| 8–10 | 3.82 ± 0.51 | 5.67 ± 0.27 | 1.69 ± 0.29 | 3.36 ± 0.75 | ND | ND |

[1]Determined 6 days after planting by dilution plating on selective media. Values are means of three replicates followed by the standard error. Inoculum populations on seeds at the time of planting were $2.7 \times 10^7$, $1.9 \times 10^7$, and $5.5 \times 10^8$ CFU/seed for *F. balustinum* 299R, *P. putida* 315R, and *X. maltophilia* 76R, respectively.
[2]Not detectable (<50 CFU/cm root).

TABLE 15

Colonization of the non-rhizosphere container medium (CHB) by bacterial antagonists introduced with inoculated seeds in a container medium pre-treated with various temperature

| | Log CFU/g dry st container medium[1] | | | | | |
|---|---|---|---|---|---|---|
| Depth (cm) in | Autoclaved | | Heated (60 C, 5 days) | | Control (25 C) | |
| container medium | Not irrigated | Irrigated | Not irrigated | Irrigated | Not irrigated | Irrigated |
| (a) *Flavobacterium balustinum* 299R | | | | | | |
| 0–2 | 8.17 ± 0.31 | 9.07 ± 0.18 | 5.66 ± 0.44 | 7.48 ± 0.03 | 3.91 ± 0.23 | 5.37 ± 0.19 |
| 6–8 | 1.70 ± 0.30 | 8.78 ± 0.20 | ND[2] | 6.44 ± 0.14 | ND | 3.07 ± 0.30 |
| 12–14 | 1.96 ± 0.56 | 8.81 ± 0.12 | ND | 6.17 ± 0.11 | ND | 2.95 ± 0.06 |
| (b) *Pseudomonas putida* 315R | | | | | | |
| 0–2 | 8.68 ± 0.20 | 8.71 ± 0.05 | 5.32 ± 0.28 | 6.69 ± 0.15 | 3.80 ± 0.28 | 4.43 ± 0.07 |
| 6–8 | 7.17 ± 0.42 | 8.22 ± 0.06 | ND | 6.04 ± 0.15 | ND | 3.06 ± 0.21 |
| 12–14 | 2.00 ± 0.46 | 7.50 ± 0.34 | ND | 6.06 ± 0.10 | ND | 2.84 ± 0.12 |
| (c) *Xanthomonas maltophilia* 76R | | | | | | |
| 0–2 | 6.70 ± 0.45 | 9.70 ± 0.03 | 5.08 ± 0.39 | 7.49 ± 0.07 | 4.55 ± 0.63 | 4.74 ± 0.06 |
| 6–8 | ND | 9.53 ± 0.12 | ND | 7.07 ± 0.06 | ND | 3.61 ± 0.09 |
| 12–14 | ND | 9.42 ± 0.05 | ND | 6.67 ± 0.12 | ND | 3.07 ± 0.03 |

[1]Determined 7 days after planting by dilution plating on selective media. Values are means of three replicates followed by the standard error. Mean inoculum populations on seeds at the time of planting were $2.7 \times 10^7$, $1.9 \times 10^7$ and $5.5 \times 10^8$ CFU/seed for *F. balustinum* 299R, *P. putida* 315R and *X. maltophilia* 76R, respectively.
[2]Not detectable (<50 CFU/g dry wt. container medium).

Lower population levels were established in the conducive CHB$_{60}$ container medium. Finally, in the suppressive CHB$_{25}$ container medium, irrigation established low population levels throughout the pots. Similar results were obtained in a second experiment with these mutants.

Survival of antagonists in the container medium. Population development of *F. balustinum* 299R, *P. putida* 315R, *X. maltophilia* 76R and *T. hamatum* 382 during 28 days after planting of radish seeds were followed. In the autoclaved container medium, the bacterial antagonists established highest population levels within 7 days after planting. Thereafter, populations declined to $10^6$–$10^7$ CFU/g dry weight. In the conducive CHB$_{60}$ container medium, lower populations developed, but all remained at levels above $10^6$ CFU/g dry weight. In the suppressive CHB$_{25}$ container medium, populations did not increase, but declined to $10^5$ CFU/g dry weight or less. In the CHB$_{60}$ treatment, to which the mutant bacterial antagonists and *T. hamatum* 382 were added simultaneously, bacterial population development was not different from that in the absence of *T. hamatum* 382.

In the autoclaved container medium, population development of *T. hamatum* 382 reached a peak after 14 days and declined thereafter. Lower populations were established in the conducive CHB$_{60}$ container medium. In the suppressive CHB$_{25}$ container medium, population levels did not change. One week after the addition of *F. balustinum* 299R in combination with *T. hamatum* 382, a slightly higher population level of *T. hamatum* 382 was added. Thereafter, the presence of *F. balustinum* 299R had no effect on *T. hamatum* 382 population development.

Survival of antagonists in natural compost. Population developments of *F. balustinum* 299R and of *T. hamatum* 382 as single and as combination antagonist treatments in container media prepared with compost removed from the suppressive edge (CHB$_e$ and conducive center (CHB$_c$) are presented in FIG. 1. In FIG. 1 are presented the population development of *Flavobacterium balustinum* 299R (—) and *T. hamatum* 382 (- - -) in a container medium planted with cucumber and amended with compost from the edge of a pile after 4 months of curing. *F. balustinum* and *T. hamatum* were inoculated individually in a container medium amended with (1) conducive compost from the high temperature center of the curing pile (O); (2) suppressive edge compost (■); or (3) were introduced as a combination treatment in the conducive center compost medium (●). Vertical bars indicate standard error. High population levels (approximately $10^8$ CFU/g dry wt.) of *F. balustinum* 299R were established within 2 days after infestation of the CHB$_c$ container medium. Thereafter, populations declined to levels found previously in the CHB$_{60}$ container medium. In the suppressive CHB$_e$ container medium, high populations also developed, which was followed by a decline. *T. hamatum* 382 on the other hand, continued to increase in population level in both the CHB$_c$ and CHB$_e$ container media. *T. hamatum* 382 again did not affect *F. balustinum* 299R population development. However, *F. balustinum* 299R increased *T. hamatum* 382 population development, as observed earlier in the CHB$_{60}$ container medium. Similar results on survival of antagonists were obtained in a second experiment with natural compost.

The results with antagonists in both sludge and bark compost media presented in Tables 10-12 are illustrative. A number of bacterial antagonists were more effective than *T. hamatum* 382 by itself. Single antagonist treatments, however, did not consistently induce suppression. Combinations of most any of the bacterial antagonists with *T. hamatum* 382 were the most efficacious treatments. The most effective treatments were combination of this Trichoderma isolate with any of the following specific bacterial strains: *Erwinia cloacae* 313, *Flavobacterium balustinum* 299, *Pseudomonas putida* 315 and *Pseudomonas stutzeri* 280. These combinations were effective in container media amended with either composted municipal sludge or composted bark. Adequate levels of suppression were established in either medium after these microorganisms were introduced at population levels of at least $10^2$ CFU/g dry weight and most desirably and preferably of $10^4$ and $10^7$ CFU/g dry weight container medium for the Trichoderma and bacterial antagonists, respectively.

The levels of suppression induced by the combination treatments to both Pythium and Rhizoctonia damping-off ranged from disease severity ratings as low as 1.1 (Pythium damping-off with *F. balustinum* 299 and *T. hamatum* 382 in Table 12) to a high of 2.7 (Rhizoctonia damping-off with *P. fluorescens* A498 and *T. hamatum* 382 in Table 11).

Several of the bacterial species listed in Tables 10, 11 and 14, i.e. *F. balustinum, J. lividium, P. stutzeri* and *X. maltophilia*, have not been reported previously as biocontrol agents for soilborne plant pathogens. *E. cloacae, P. putida* and *P. fluorescens* are reported most frequently as beneficial rhizobacterial (Drahos et al., Biotechnology 4: 439-444, 1986).

Population development of selected bacterial strains in the presence or absence of a *T. hamatum* strain was followed with spontaneous, rifampicin-resistance mutants. Effective strains of *F. balustinum* and *P. putida* colonized cucumber roots and container media, whether applied as seed treatment or as inoculum to the container medium. Highest population levels were reached within 2 weeks after inoculation. In media prepared with suppressive edge-compost their population development was suppressed. Population development of the introduced *Trichoderma hamatum* strain was not suppressed in the presence of the bacterial antagonists. In some experiments, this population development was enhanced by the presence of *F. balustinum*.

In further experiments of interest to the foregoing disclosure and examples, there were discovered some important parameters for practicing effective preparation and employment of container media amended with sewage sludge. Container media formulated with composted municipal sludge cured 4 months or more were utilized without phytotoxicity problems to radish or cucumber seedlings and a wide range of greenhouse and nursery crops. Composted municipal sludge, produced in an aerated bioreactor or by the aerated static pile method and cured less than 3 months thereafter, had objectionable odor problems during the formulation of container media. Such problems were not encountered with composts cured 4 months or more.

Greenhouse container media amended with 4 months cured composed municipal sludge (25% v/v) and nursery container media amended with 20% (v/v), suppressed both Rhizoctonia and Pythium diseases over 5 months and 2-year production cycles, respectively. However, suppressiveness of sludge compost media to both diseases varied unless certain precautions were taken. The curing process affected suppressiveness. Pythium damping-off on cucumber was suppressed in sludge compost media if prepared with compost from curing piles with temperatures in the center of the pile <60° C. (after more than 4 weeks of curing). Rhizoctonia damping-off was not suppressed in media prepared with compost cured less than 8 weeks in 2.2 m high piles. Media prepared with compost cured 4 months or more in large curing piles (5-6 m high) without turning, also were consistently conducive initially after their formulation. However, all media prepared with sludge compost cured 4 months or more and stored 4 weeks after their formulation became consistently suppressive. The levels of suppression were adequate to avoid losses under commercial conditions. The beneficial microflora involved in suppression, if present, survived in the outer low temperature layer of curing piles only. Canadian sphagnum peat used in the formulation of sludge compost media, was not a reliable source of inoculum for this beneficial microflora. It was concluded that composted municipal sludge should be cured at least 4 months before utilization and that its amended container media be stored at least 1 month before potting to ensure suppressiveness to both Rhizoctonia and Pythium diseases. Much of the compost curing time and all of the container medium storage requirement can be eliminated by the controlled inoculation of compost or the compost-amended medium with antagonists disclosed earlier.

It will be apparent to those skilled in the art that numerous changes and improvements can be made in the preferred embodiments of the invention described above without departing from the scope of the invention. Accordingly, the foregoing description is to be construed in an illustrative and not in a limitative sense, the scope of the invention being defined solely by the appended claims.

I claim:

1. A method for producing a container medium which is suppressive to at least *Rhizoctonia solani* and *Pythium ultimum* and/or diseases caused thereby, which method comprises: amending the container medium so that each 100 parts thereof includes about 2.5 to 70 parts by volume of compost and at least one Trichoderma fungus antagonistic to *Rhizoctonia solani* and suppressive to plant disease caused thereby and at least one bacterium antagonistic to *Pythium ultimum* and suppressive to plant disease caused thereby with the amending including at least 100 colony forming units each of the fungus and the bacterium for each gram dry weight of the compost.

2. The method of claim 1 in which the amending of the container medium is with the compost which before the amending had been inoculated with said at least one fungus and said at least one bacterium in the amount of each of at least 100 colony forming units for each gram dry weight of the compost.

3. The method of claim 2 employing hardwood tree bark for the compost.

4. The method of claim 2 employing pine bark for the compost.

5. The method of claim 2 employing sewage sludge for the compost.

6. The method of claim 2 employing the compost which had been inoculated after peak heating had been achieved but before substantial recolonization of said compost by mesophilic microorganism had occurred.

7. The method of claim 2 in which the at least one Trichoderma fungus is selected from the group consisting of *Trichoderma hamatum* isolates 382, A.T.C.C. No. 20765, and 599, A.T.C.C. No. 20764, and the at least one bacterium is selected from the group consisting of *Flavobacterium balustinum* isolate 299, A.T.C.C. No. 53198, *Xanthomonas maltophilia, (Pseudomonas maltophilia)* isolate 76, A.T.C.C. No. 53199, *Pseudomonas putida* isolate 315, A.T.C.C. No. 53915, their spontaneous rifampicin resistant mutants, *Pseudomonas stutzeri* isolate 280, A.T.C.C. No. 53917, and *Pseudomonas fluorescens* biovar V isolate A498, A.T.C.C. No. 53916.

8. The method of claim 2 which employs *Trichoderma hamatum* isolate 382, A.T.C.C. No. 20765 and *Flavobacterium balustinum* isolate 299 A.T.C.C. No. 53198.

9. The method of claim 1 in which the container medium is amended separately with the compost and with said Trichoderma fungus and said bacterium separately or mixed together.

10. The method of claim 9 employing hardwood tree bark for the compost.

11. The method of claim 9 employing pine bark for the compost.

12. The method of claim 9 employing sewage sludge for the compost.

13. The method of claim 9 in which the at least one Trichoderma fungus is selected from the group consisting of *Trichoderma hamatum* isolates 382, A.T.C.C. No. 20765, and 599, A.T.C.C. No. 20764, and the at least one bacterium is selected from the group consisting of *Flavobacterium balustinum* isolate 299, A.T.C.C. No. 53198, *Xanthomonas maltophilia (Pseudomonas maltophilia)* isolate 76, A.T.C.C. No. 53199, *Pseudomonas putida* isolate 315 A.T.C.C., No. 53915, their spontaneous rifampicin resistant mutants, *Pseudomonas stutzeri* isolate 280, A.T.C.C. No. 53917, and *Pseudomonas fluorescens* biovar V isolate A498, A.T.C.C. No. 53916.

14. The method of claim 9 which employs *Trichoderma hamatum* isolate 382, A.T.C.C. No. 20765, and *Flavobacterium balustinum* isolate 299 A.T.C.C. No. 53198.

15. A biologically pure culture consisting essentially of any one or more of the following microorganisms:
*Pseudomonas putida* isolate 315, A.T.C.C. No. 53915;
*Pseudomonas stutzeri* isolate 280, A.T.C.C. No. 53917;
*Pseudomonas fluorescens* biovar V isolate A498, A.T.C.C. No. 53916;
and the spontaneous rifampicin resistant mutants of each of:
*Flavobacterium balustinum* isolate 299, A.T.C.C. No. 53198
*Pseudomonas maltophilia (Xanthomonas-maltophilia)* isolate 76, A.T.C.C. No. 53199, and
*Pseudomonas putida* isolate 315, A.T.C.C. No. 53915.

16. A biologically pure culture for inducing suppression of plant pathogens and/or diseases caused thereby, which said culture consists essentially of at least one Trichoderma fungus selected from the group consisting of *Trichoderma hamatum* isolates 382, A.T.C.C. No. 20765, and 599, A.T.C.C. No. 20764 and at least one bacterium selected from the group consisting of:
*Pseudomonas putida* isolate 315, A.T.C.C. No. 53915;
*Pseudomonas stutzeri* isolate 280, A.T.C.C. No. 53917;
*Pseudomonas fluorescens* biovar V isolate A498, A.T.C.C. No. 53916;
and the spontaneous rifampicin resistant mutants of each of:
*Flavobacterium balustinum* isolate 299, A.T.C.C. No. 53198
*Pseudomonas maltophilia (Xanthomonas-maltophilia)* isolate 76, A.T.C.C. No. 53199, and
*Pseudomonas putida* isolate 315, A.T.C.C. No. 53915.

* * * * *